(12) United States Patent
Jensen et al.

(10) Patent No.: US 7,651,690 B2
(45) Date of Patent: Jan. 26, 2010

(54) PURIFIED COMPONENT OF BLUE-GREEN ALGAE AND METHOD OF USE

(75) Inventors: Gitte S. Jensen, Ontario (CA); Christian Drapeau, Ashland, OR (US)

(73) Assignee: Desert Lake Technologies, Keno, OR (US)

( * ) Notice: Subject to any disclaimer, the term of this patent is extended or adjusted under 35 U.S.C. 154(b) by 178 days.

(21) Appl. No.: 11/473,875

(22) Filed: Jun. 23, 2006

(65) Prior Publication Data
US 2007/0003647 A1 Jan. 4, 2007

Related U.S. Application Data

(60) Provisional application No. 60/700,882, filed on Jul. 19, 2005, provisional application No. 60/693,808, filed on Jun. 24, 2005.

(51) Int. Cl.
*A61K 36/02* (2006.01)
(52) U.S. Cl. .................................. 424/195.17
(58) Field of Classification Search ........................ None
See application file for complete search history.

(56) References Cited

U.S. PATENT DOCUMENTS

| 6,814,961 B1 | 11/2004 | Jensen et al. |
| 7,205,284 B2 | 4/2007 | Pasco et al. |

FOREIGN PATENT DOCUMENTS

| WO | WO02/04000 | 1/2002 |
| WO | WO 2004/066969 | 8/2004 |

OTHER PUBLICATIONS

Benedetti et al. (Life Sciences (Sep. 2004), pp. 2353-2362).*
Kumar et al. (Indian Journal of Microbiology (2003), vol. 43, No. 1, pp. 9-16).*
Kumar et al., "Bioregulatory and therapeutic effects of blue green algae," *Indian J. Microbiology* 43(1):9-16, Mar. 2003.
Barrett, "StemTech's Dubious Claims," http://www.mlmwatch.org/04C/Stemtech/stemtech.html (4 pages), downloaded Jun. 13, 2006.
Drapeau, "Triple-Blind Randomized Placebo-Controlled Study of the Effect of StemEnhance on Bone Marrow Stem Cell Mobilization." StemTech HealthSciences, Inc., online at http://www.brightbeing.stemtechhealth.com (3 pages), downloaded Jun. 23, 2006.
Pugh, et al., "Isolation of Three High Molecular Weight Polysaccharide Preparations with Potent Immunostimulatory Activity from *Spirulina platensis, Aphanizomenon flos-aquae* and *Chlorella pyrenoidosa,*" Planta Med 67:737-742 (2001).
"StemEnhance™ The first Stem Cell Enhancer" published by StemTech HealthSciences, Inc., http://www.stemtechhealth.com, 1 page, downloaded Jun. 13, 2006.
"Adult Stem Cells Enhancement, New Breakthrough Product: StemEnhance™ from StemTech Health Sciences, Inc.," http://www.astrologyzine.com/stemtech-stemenhance-stem-cell-enhancer.shtml (9 pages), downloaded Jun. 13, 2006.

Bhat and Madyastha, "C-Phycocyanin: A Potent Peroxyl Radical Scavenger in Vivo and in Vitro," *Biochemical and Biophysical Research Communications*, 275:20-25, 2000.
Cousens, G., "Report of Treatment of Alzheimer's Disease with Alphanae Klamathomenon Flos-Aqua," *Orthomedicine*, 8:(1 & 2), 2000.
González et al., "Anti-Inflammatory Activity of Phycocyanin Extract in Acetic Acid-Induced Colitis in Rats," *Pharmacological Research*, 39(1):55-59, 1999.
Jensen et al., "Consumption of Aphanizomenon flos-aquae Has Rapid Effects on the Circulation and Function of Immune Cells in Humans," *JANA*, 2(3):50-58, 2000.
Kushak, et al., "Favorable Effects of Blue-Green Algae *Aphanizomenon flox-aquae* on Rat Plasma Lipids," *JANA*, 2(3):59-65, 2000.
Kushak, et al., "The Effect of Blue-Green Algae *Aphanizomenon Flos-Aquae* on Nutrient Assimilation in Rats," *JANA*, 3(4):35-39, 2001.
Lahitová et al., "Antimutagenic Properties of Fresh-Water Blue-Green Algae," *Folia Microbiol.*, 39(4):301-303, 1994.
Ostensvik et al., "Antibacterial properties of extracts from selected planktonic freshwater cyanobacteria—a comparative study of bacterial bioassays," *Journal of Applied Microbiology*, 84:1117-1124, 1998.
Pugh and Pasco, "Characterization of human monocyte activation by a water soluble preparation of *Aphanizomenon flos-aquae,*" *Phytomedicine*, 8(6):445-453, 2001.
Reddy et al., "Selective Inhibition of Cyclooxygenase-2 by C-Phycocyanin, a Biliprotein from *Spirulina platensis,*" *Biochemical and Biophysical Research Communications*, 277:599-603, 2000.
Remirez et al., "Effect of Phycocyanin in Zymosan-Induced Arthritis in Mice—Phycocyanin as an Antiarthritic Compound," *Drug Development Research*, 48:70-75, 1999.
Rimbau et al., "Protective effects of C-phycocyanin against kainic acid-induced neuronal damage in rat hippocampus," *Neuroscience Letters*, 276:75-78, 1999.
Rimbau et al., "C-Phycocyanin protects cerbellar granule cells from low potassium/serum deprivation-induced apoptosis," *Naunyn-Schmiedeberg's Arc Pharmacol*, 364:96-104, 2001.
Romay and González, "Phycocyanin is an Antioxidant Protector of Human Erythrocytes Against Lysis by Peroxyl Radicals," *J. Pharm. Pharmacol.*, 52:367-368, 2000.
Romay et al., "Antioxidant and anti-inflammatory properties of C-phycocyanin from blue-green algae," *Inflamm. Res.*, 47:36-41, 1998.

(Continued)

*Primary Examiner*—Susan C Hoffman
(74) *Attorney, Agent, or Firm*—Klarquist Sparkman, LLP

(57) ABSTRACT

Disclosed herein are extracts of blue green algae, such as *Aphanizomenon flos aquae*, that are enriched for a selectin ligand, such as an L-selectin ligand. Selectin ligands isolated from blue-green algae cells are disclosed herein. Methods are described for isolating these selectin ligands. The purified selectin ligands are of use in inducing stem cell mobilization in a subject. Thus, methods for inducing stem cell isolation that include administering a therapeutically effective amount of the extract enriched form the selectin ligand, or an isolated selectin ligand, are disclosed herein.

14 Claims, 9 Drawing Sheets

OTHER PUBLICATIONS

Romay et al., "Further studies on anti-inflammatory activity of phycodyanin in some animal models of inflammation," *Inflamm. Res.*, 57:334-338, 1998.

Romay et al., "Phycocyanin Extract Reduces Leukotriene $B_4$ Levels in Arachidonic Acid-induced Mouse-ear Inflammation Test," *J. Pharm. Pharmocol.*, 51:641-642, 1999.

Romay et al., "Effects of Phycocyanin Extract on Prostaglandin $E_2$ Levels in Mouse Ear Inflammation Test," *Arzneim.-Forsch./Drug Res.* 50(II), 1106-1109, 2000.

Schaeffer and Krylov, "Anti-HIV Activity of Extracts and Compounds from Algae and Cyanobacteria," *Ecotoxicology and Environmental Safety*, 45:208-227, 2000.

Vadiraja et al., "Hepatoprotective Effect of C-Phycocyanin: Protection for Carbon Tetrachloride and R-(+)-Pulegone-Mediated Hepatotooxicty in Rats," *Biochemical and Biophysical Research Communications*, 249:428-431, 1998.

\* cited by examiner

Table 1. AFA-W blocks binding of TQ1 MoAb to L-selectin on human leukocytes.

|  | Lymphocytes | | | Neutrophils |
| --- | --- | --- | --- | --- |
|  | Unfixed cells | 0.02% sodium azide | 1% formalin | 1% formalin |
| Mean fluorescence | | | | |
| Unstained cells | 1 | 1 | 1 | 2 |
| TQ1 staining | 244 | 366 | 149 | 156 |
| TQ1 staining after AFA-W pre-treatment | 98 | 216 | 82 | 61 |
| t-test | <0.003 | <0.002 | <0.005 | <0.001 |
| Median fluorescence | | | | |
| Unstained cells | 1 | 1 | 1 | 1 |
| TQ1 staining | 221 | 374 | 134 | 138 |
| TQ1 staining after AFA-W pre-treatment | 44 | 208 | 64 | 26 |
| t-test | <0.002 | <0.001 | <0.02 | <0.001 |

All staining was performed in triplicate. Values given for stained cells are based on averages from 3 samples.

PURIFIED COMPONENT OF BLUE-GREEN ALGAE AND METHOD OF USE

CROSS REFERENCE TO RELATED APPLICATIONS

This application claims the benefit of U.S. Provisional Application No. 60/693,808, filed Jun. 24, 2005, and U.S. Provisional Application No. 60/700,882, filed Jul. 19, 2005. Both of the provisional applications are incorporated by reference herein in their entirety.

FIELD

This application relates to an aqueous extract from blue-green algae, such as an aqueous extract of algae that includes a selectin ligand.

BACKGROUND

Stem cells are pluripotent cells derived from somatic tissue capable of differentiating into more specialized cells. For example, hematopoietic stem cells can differentiate into many different types of blood cells, including red blood cells, platelets, and leukocytes.

Hematopoietic stem cells play a role in the continuous lifelong physiological replenishment of blood cells. Stem cells develop into both hematopoietic lineage cells and non-hematopoietic, tissue specific cells. Recently, stem cells have been found to differentiate into a variety of tissue-specific cell types, such as myocytes, hepatocytes, osteocytes, glial cells, and neurons. For example, stem cells have been shown to cross the blood-brain barrier (Willams and Hickey, *Curr. Top. Microbiol. Immunol.* 202:221-245, 1995) and differentiate into neurons (Mezey, *Science* 290:1779-82, 2000). Thus, it is possible that stem cells could be used to treat Parkinson's disease (Polli, *Haematologica* 85:1009-10, 2000), Alzheimer's disease (Mattson, *Exp. Gerontol.* 35:489-502, 2000), and traumatic brain injury (Magavi, *Nature* 405: 892-3, 895, 2000). Stem cells also have been shown to differentiate into fibroblasts or fibroblast-like cells, and to express collagen (Periera et al., *Proc. Natl. Acad. Sci.* 95:1142-7, 1998). Thus, it is possible that stem cells can be used to treat osteogenesis imperfecta and bone fractures. Peterson et al. (*Science* 284: 1168-70, 1999) also has shown that liver cells can arise from stem cells. Thus, stem cells may be of use in treating a variety of pathologies of the liver, including, but not limited to cirrhosis. In addition, bone marrow derived stem cells have been demonstrated to migrate to the site of a myocardial infarction and form myocardium (Orlic, *Nature* 410:701-5, 2000). Thus, stem cells may be use in treating myocardial infarction.

Since stem cells are capable of differentiating into a broad variety of cell types, they play an important role in the healing and regenerative processes of various tissues and organs (see Koc et al., *Bone Marrow Transplant,* 27(3):235-39, 2001). Selectin ligands stimulate the release of stem cells from the bone marrow (Frenette et al., *Blood* 96:2460-68, 2000).

Many studies suggest that the mobilization, migration and differentiation of bone marrow stem cells in the target tissue constitute a natural phenomenon of healing in the human body (Spencer et al., *Thorax* 60(1):60-2, 2005; Ishikawa et al., *FASEB J.* 18(15):1958-60, 2004; Mattsson et al., *Transplantation* 15; 78(1):154-7, 2004; Thiele Jet al., *Transplantation* 77(12):1902-5, 2004; Cogle et al., *The Lancet* 363 (9419):1432-7, 2004; Deb et al., *Circulation* 107(9):1247-9, 2003; Korbling et al., *N Engl J Med* 346(10):738-46, 2002; Adams et al., *Blood* 102(10):3845-7, 2002; Krause et al., *Cell* 105(3):369-77, 2001). Mobilized stem cells follow concentration gradients of cytokines released by damaged tissues and migrate on their own into tissues following such gradients. Indeed, the mobilization of bone marrow stem cells induced by cytokines injection has been shown to accelerate the healing the cardiac tissue after acute myocardial infarction. Therefore, simply triggering the mobilization of bone marrow stem cells with an effective and safe consumable can enhance this natural physiological process and provide a potential therapy for various pathologies. Thus, there is a need for compositions that increase stem cell mobilization and trafficking.

SUMMARY

An exemplary procedure is disclosed for obtaining an aqueous extract of blue-green algae containing a selectin ligand. In this procedure, a selectin ligand is isolated from blue-green algae using a solid substrate covalently bound to a selectin, such as L-selectin, P-selectin, and/or E-selectin. The selectin ligand can specifically bind L-selectin, P-selectin and/or E-selectin.

Purified selectin ligands that are isolated from blue-green algae are described. These ligands are isolated from blue-green algae that are a protein or a glycoprotein of a molecular weight of about 55 kDa under reducing conditions. In several examples, the selectin ligand has a molecular weight of about 54 kDa or about 57 kDa under reducing conditions. In additional examples, selectin ligand has a molecular weight of about 54 kDa, about 57 kDa, about 162 kDa, about 171 kDa, about 233 kDa or about 111 kDa under non-reducing conditions.

An extract of *Aphanizomenon flos aquae* (AFA) is disclosed herein that contains L-selectin ligand. This extract can be formulated for administration to a subject. Compositions including the extract alone, or including other extracts of *Aphanizomenon flos aquae* (AFA) can be administered to a subject in need of stem cell mobilization and/or increased number of circulating stem cells. In one example, the extract containing the L-selectin ligand is administered with an extract of *Aphanizomenon flos aquae* (AFA) containing polysaccharides. Compositions, which include or consist of the L-selectin ligand of *Aphanizomenon flos aquae* (AFA) are of use for stem cell mobilization and increasing the number of circulating stem cells.

A method is disclosed herein for triggering stem cell mobilization by administering a therapeutically effective amount of a specific extract of blue-green algae to a subject. Extracts of use in inducing stem cell mobilization include extracts of blue-green algae containing a selectin ligand, such as an L-selectin, P-selectin and/or an E-selectin ligand. In one example, the blue-green algae is *Aphanizomenon flos aquae* (AFA). The extracts can be administered alone or in conjunction with other extracts of *Aphanizomenon flos aquae* (AFA). In one example, a polysaccharide containing extract is also administered.

The administration of a therapeutically effective amount of an extract of the blue-green algae, such as a selectin ligand containing extract, induces a transient increase in the population of some stem cells, such as CD34+ stem cells and/or CD133+ stem cells, in the subject's circulatory system.

The foregoing and other features and advantages will become more apparent from the following detailed description of several embodiments, which proceeds with reference to the accompanying figures.

BRIEF DESCRIPTION OF THE FIGURES

FIG. 4A is a digital image that shows the compound eluted from beads that were coated with human recombinant L-selectin, and FIG. 4B is a digital image that shows the compound eluted from beads coated with human recombinant P-selectin. The gels were run under reducing conditions. Two distinct bands at approximately 54 and 57 kDa are shown. Identical band patterns were seen for both L- and P-selectin, indicating that the selectin ligand is a ligand for both L- and P-selectin.

FIG. 7 is a line graph showing the results from a flow cytometry analysis of the expression of the chemokine receptor CXCR4, as it is induced by a known L-selectin ligand, Fucoidan. The data indicates that the known L-selectin ligand Fucoidan, competes with the compound from AFA for binding to L-selectin on the human CD34+ cell line KG-1a.

FIG. 8 is a Table. The results presented show that Extract A (AFA-W) blocks binding of TQ1 MoAb to L-selectin on human leukocytes.

DETAILED DESCRIPTION

I. Abbreviations

Figure 1:
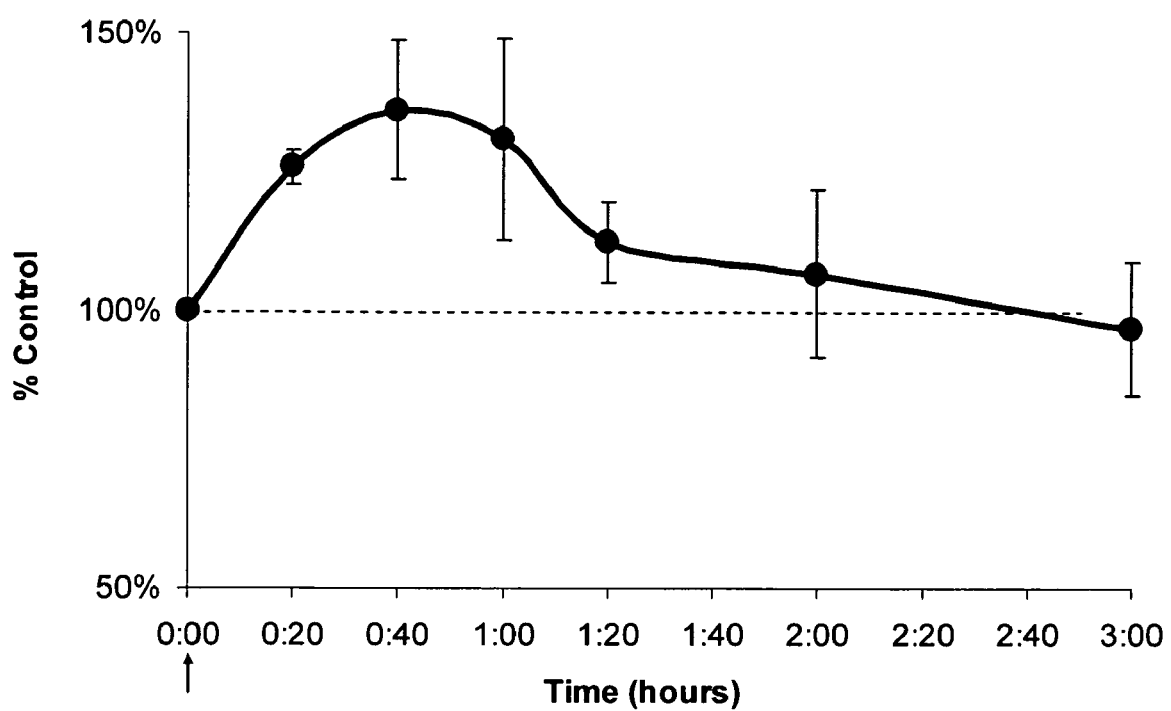
FIG. 1 is line graph showing a time course for increase in the number of circulating stem cells in the blood of healthy humans upon ingestion of AFA. Flow cytometry was performed on human lymphocytes and monocytes, where the monoclonal antibody CD34, with specificity for human stem cells was used to demonstrate that AFA extract A contains a compound that mobilizes stem cells by increasing their numbers in the blood circulation.

AFA: *Aphanizomenon flos aquae*
Ctrl: control
LSL: L-selectin ligand
mg: milligram
ml: milliliter
MGT: migratose
SE: stem enhance combination, includes LSL and MGT
g: gram
kg: kilogram II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration to a subject. Providing blue-green algae to a subject includes administering whole blue-green algae cells and/or extracts (fractions) of blue-green algae cells. Routes of administration include, but are not limited to, oral and parenteral routes, such as intravenous (IV), intraperitoneal (IP), rectal, topical, ophthalmic, nasal, and transdermal. Oral administration includes both whole blue-green algae and extracts of blue-green algae. More than one extract can be administered. If administered orally, the whole cells or extracts may be provided or administered in the form of a unit dose in solid, semi-solid, or liquid dosage form such as tablets, pills, powders, liquid solutions, or liquid suspensions. However, extracts of blue-green algae also may be administered intravenously in any conventional medium for intravenous injection, such as an aqueous saline medium, or in a blood plasma medium. The medium also may contain conventional pharmaceutical adjunct materials, such as pharmaceutically acceptable salts to adjust the osmotic pressure, lipid carriers (e.g., cyclodextrins), proteins (e.g., serum albumin), hydrophilic agents (e.g., methyl cellulose), detergents, buffers, preservatives, and the like. A more complete explanation of acceptable pharmaceutical carriers can be found in *Remington: The Science and Practice of Pharmacy* ($19^{th}$ Edition, 1995) in chapter 95.

Agent that affects hematopoiesis. A compound, antibody, nucleic acid molecule, protein, glycoprotein, or cell that alters the formation of blood cells, such as white blood cells. A molecular agent can be a naturally occurring molecule or a synthetic molecule. In some embodiments, the agent affects the mobilization, growth, proliferation, maturation, or differentiation or release of hematopoietic cells. In one embodiment, the agent is a selectin ligand extracted from a blue-green algae cell.

Agent that affects stem cell circulation. A compound, antibody, nucleic acid molecule, protein, glycoprotein, or cell, including neuropeptides and other signaling molecules, that affects the release of stem cells into the circulatory system, as well as homing from the circulatory system into tissue. A molecular agent may be a naturally occurring molecule or a synthetic molecule. In one specific example, the agent is a selectin ligand from blue-green algae.

An agent that affects stem cell circulation may affect the ratio of stem cells in the quiescent pool versus the active pool. In some embodiments, the agent affects the balance between undifferentiated stem cells and stem cells differentiating into CD34– negative (CD34–) and CD34-positive (CD34+) cell, and/or CD133-negative (CD133–) and CD133-positive (CD133+) cells. In other embodiments, the agent affects the release of stem cells from tissue locations, such as the release of CD34+ cells and/or CD133+ cells and/or cells detected by methods based on the enzymatic actions of aldehyde dehydrogenase, from the bone marrow environment.

Animal. A living, multicellular, vertebrate organism including, for example, mammals, fish, reptiles, and birds.

Blue-green algae. Common name for gram-negative photosynthetic bacteria belonging to Division Cyanophyta that may exist in unicellular, colonial, or filamentous forms. Representative blue-green algae include, but are not limited to, *Spirulina* species and *Aphanizomenon* species. *Aphanizomenon flos aquae* (AFA) is one specific, non-limiting type of blue-green algae.

The term "algae" is the plural form of "alga," which is a cell of a microalgae species. For example (and without limitation), "blue-green algae" refers to multiple cells of a single *Aphanizomenon* species, multiple cells of a single *Spirulina* species, or a mixture of cells from multiple *Aphanizomenon* and/or *Spirulina* species.

Circulatory system. In animals, the circulatory system is composed of the structures that move blood and blood components throughout the body, including the vascular and lymph systems. The components of the circulatory system include the heart, blood vessels (arteries, veins, and capillaries), and lymph vessels.

Circulating stem cell. A stem cell present in the circulatory system.

Component of blue-green algae. Any fraction, extract, or isolated or purified molecule from a blue-green algae cell. In one embodiment, the component is a protein or a glycoprotein or nucleic acid. In another embodiment, the component is a component is a phytochemical. In another embodiment, the component is an aqueous extract of a blue-green algae including a selectin ligand. Thus, the blue-green algae is disrupted, an inorganic or organic solvent is added, and extracts are collected. Specific, non-limiting examples are extracts isolated using high performance liquid chromatography, thin layer chromatography, affinity column, magnetic beads or distillation. In one embodiment, fractionation is based on the molecular weight or the hydrophobicity of the components of the blue-green algae.

Differentiation. The process by which cells become more specialized to perform biological functions. Differentiation is a property that is often totally or partially lost by cells that have undergone malignant transformation.

Effective amount. An amount, such as an amount of a selectin-containing extract of blue-green alga, capable of triggering or enhancing stem cell mobilization, which can be determined by various methods used in the biological sciences. These methods include, but are not limited to, generating an empirical dose-response curve. In one embodiment, a "therapeutically effective amount" is an amount effective for enhancing mobilization of stem cells that replenish, repair, or rejuvenate tissue. In another embodiment, a "therapeutically effective amount" is an amount effective for enhancing trafficking of stem cells. In still another embodiment, the "therapeutically effective amount" is an amount effective for enhancing homing of stem cells from the circulatory system to various tissues or organs.

A therapeutically effective amount also may be an amount sufficient for treating a condition or disease, such as an amount sufficient to relieve symptoms associated with nervous system disorders (for example, Alzheimer's disease, Parkinson's disease, multiple sclerosis), traumatic brain or spinal cord injury, liver disease, or disorders of bone or cartilage. A therapeutically effective amount may also be an amount sufficient for accelerating and enhancing the recovery from acute myocardial infarction.

In one specific, non-limiting example, the therapeutically effective amount of the extract, such as a selectin-containing extract of blue-green algae, is from about 0.01 to about 1.0 g per kg body weight, such as about 0.05 to about 0.5 gram per kg body weight, or from about 0.1 to about 0.5 gram per kg body weight. In another specific, non-limiting, example the effective amount of the selectin-containing extract of blue-green algae is from about 0.25 gram to about 5 gram, of from about 0.5 gram to about 5 gram, or from about 1 gram to about 2 gram. In one specific, non-limiting example, the effective amount of selectin-containing extract of blue-green algae is 1 gram. This effective amount may be administered at a given frequency, such as about once a week, about twice a week, about three times a week, once a day, about twice a day, about three times a day, or more.

The therapeutically effective amount of an extract of blue-green algae, such as a selectin-containing aqueous extract of blue-green algae and frequency of administration may depend on a variety of factors, such as the genus or species of algae utilized, the general health of the subject being treated, and the physiological characteristics (e.g., height, weight, body fat percentage, metabolism, etc.) of the subject being treated.

Specific assays for determining a therapeutically effective amount of an aqueous extract, such as a selectin ligand-containing extract, of blue-green algae are provided herein. In one specific, non-limiting example, different amounts of a selectin ligand-containing extract of blue-green algae, such as AFA, are consumed by human subjects and the presence and/or quantity of stem cells (which can include subtypes of such cells) present in the circulatory system is detected and/or analyzed. In another embodiment, an animal (e.g. murine) model is utilized, and the population of newly integrated stem cells is monitored in various tissues (see the Examples below). The methods disclosed have equal application in medical and veterinary settings. Therefore, the general term "subject being treated" includes all vertebrates (for example, but not limited to, humans, apes, dogs, cats, mice, rats, rabbits, sheep, horses, pigs, and cows).

Enhancement (enhancing). An increase in a particular parameter of a cell or organism. In one embodiment, enhancement refers to a 25%, 50%, 100% or greater than 100% increase in a parameter. In one specific, non-limiting example, enhancement of stem cell circulation refers to an increase in a specific population of the cells, such as a 25%, 50%, 100%, 200%, 400%, 500%, or greater increase in the specific population of cells or the response of the population of cells. In one embodiment, the parameter is the mobilization of stem cells. In another embodiment, the parameter is the differentiation of stem cells. In yet another embodiment, the parameter is the homing of stem cells.

Erythrocytes. Red blood cells that carry oxygen to tissues of the body.

Extract. A concentrated preparation of a composition, such as a blue-green algae, obtained by removing the active constituents of the composition with suitable solvents, evaporating all or nearly all of the solvent, and adjusting the residual mass or powder to the a pre-determined standard amount. An extract is "enriched" for a product, such as a selectin ligand, if the activity or amount of a component of interest is increased substantially in the extract as compared to other extracts or to the same amount of the extracted original composition.

Glycoprotein. A complex molecule made of a protein moiety and a glycan or polysaccharide moiety.

Hematopoiesis. The formation and development of blood cells. Hematopoiesis involves the proliferation and terminal differentiation of hematopoeietic stem cells. In adult mammals, hematopoiesis is known to occur in bone marrow. Hematopoiesis is the production of hematopoietic cells including B cells, T cells, cells of the monocyte macrophage lineage, and red blood cells.

Homing. The process of a cell migrating from the circulatory system into a tissue or organ. In some instances, homing is accomplished via tissue-specific adhesion molecules and adhesion processes.

Immunologically normal. "Immunologically normal" denotes a subject that displays immune system characteristics typical for the species to which the individual belongs. These typical characteristics include, among others, functioning B cells and T cells as well as structural cell components, called cell surface antigens, which act as the immunologic signature for a particular organism.

The use of such immunologically normal recipients means that an immunologically normal recipient's immune system, via its B (humoral response) and T (cellular response) cells, will identify the cell surface antigens of a foreign cell or an engrafted tissue as foreign. This recognition leads ultimately to an immune response against the cell or tissue, resulting in destruction of the cell or rejection of the graft. An immune response against an allogeneic tissue is known as host-versus-graft rejection.

Immunologically compromised. An "immunologically compromised" subject has a genotypic or a phenotypic immunodeficiency. A genotypically-immunodeficient subject has a genetic defect that results in an inability to generate either humoral or cell-mediated responses. A specific, non-limiting example of a genotypically immunodeficient subject is a genotypically immunodeficient mouse, such as a SCID mouse or a bg/nu/xid mouse (Andriole et al., *J. Immunol.* 135:2911, 1985; McCune et al., *Science* 241:1632, 1988) or an XSCID human. A "phenotypically-immunodeficient subject" is a subject, which is genetically capable of generating an immune response, yet has been phenotypically altered such that no response is seen. In one specific, non-limiting example, a phenotypically-immunodeficient recipient is irradiated. In another specific, non-limiting example, a phenotypically-immunodeficient subject has been treated with chemotherapy. In yet another specific, non-limiting example, the phenotypically-immunodeficient subject has suffered a bacterial or viral infection, such as the human immunodeficiency virus (HIV) or simian immunodeficiency virus (SIV).

Increase: A significant increase in a particular activity or of a component of interest. In one embodiment, inhibition refers to at least about a 25%, 50%, 60%, 70%, 80%, 90%, 95% or 100% increase in activity or concentration.

Inhibit. A decrease in a particular parameter of a cell or organism. In one embodiment, inhibition refers to a 25%, 50%, or 100% decrease in a parameter.

Isolated. An "isolated" biological component (such as a nucleic acid molecule, polypeptide, polysaccharide, selectin, selectin ligand, or other biological molecule) has been substantially separated or purified away from other biological components of cells in which the component naturally occurs. An "isolated" cell has been substantially separated or purified away from other cells of different species (in the case of microorganisms) or cells of the organism (in the case of multi-cellular organisms). Nucleic acids and proteins may be isolated by standard purification methods, recombinant expression in a host cell, or chemically synthesized. Cells may be isolated by standard culturing methods. In one embodiment, the blue-green algae is harvested from a natural source (such as Klamath Lake), and prepared by drying (see below).

Leukocytes. White blood cells. Spherical, colorless, and nucleated corpuscles involved in host defense, including immunological responses. Specific types of leukocytes include basophils, coelomocytes, eosinophils, haemocytes, lymphocytes, neutrophils, and monocytes, circulating dendritic cells, and circulating hematopoietic stem cells.

L-selectin. A member of the selectin family calcium-dependent lectins, also known as CD62L. An adhesion molecule used by stem cells to adhere to the bone marrow environment. L-selectin, the smallest of the vascular selectins, is a 74-100 kDa molecule, that is constitutively expressed at the tips of microfolds on granulocytes, monocytes, and a vast array of circulating lymphocytes L-selectin is also known as LECAM-1, LAM-1, Mel-14 antigen, $gp90^{mel}$, and Leu8/TQ-1 antigen. L-selectin is known to be important for binding of leukocytes to endothelium in various physiological situations, including binding of phagocytes to endothelium, binding of leukocytes to inflamed endothelium, and lymphocyte homing and adhesion to high endothelial cells of post capillary venules of peripheral lymph nodes. Moreover, this adhesion molecule contributes greatly to the capture of circulating leukocytes during the early phases of the adhesion cascade. The amino acid sequences of many L-selectins are known.

An "L-selectin ligand" specifically binds L-selectin. In some embodiments, a ligand can block activation by other ligands, for example by spatial interference with the ligand binding area. A ligand can also activate the cell via ligation to L-selectin, for example by triggering calcium flux, cytoskeletal rearrangements, or other signaling events. In addition, a ligand can alter signal transduction pathways so a subsequent binding with either another L-selectin ligand, or an L-selectin-independent stimulus results in an altered physiological response. In some examples, when human lymphocytes are activated via some L-selectin ligands, L-selectin triggers the expression of CXCR4, a receptor for Stromal Derived Factor 1 (SDF1), a cytokine involved in the residence of stem cells in the bone marrow. In one embodiment, the L-selectin-containing extract of the blue-green algae inhibited the expression of CXCR4 triggered by the activation of L-selectin with Fucoidan. Amino acid sequences for exemplary L-selectin ligands are known. For example, Mus musculus GlyCam-1 is shown in GENBANK Accession Number NM_008134 and Human mRNA isolates for GlyCam-1 are shown in GENBANK Accession Nos. AJ_489 590, AJ 489 591, AJ 489 592, AJ 489 593, and AJ 489 589, all as available on Jun. 24, 2005, which are incorporated herein by reference. These amino acid sequences are not meant to be limiting, but are provided as examples. Recombinant and modified forms are included in the present disclosure.

Lymphocytes. A type of white blood cell that is involved in the immune defenses of the body. There are two main types of lymphocytes: B cell and T cells.

Lymphoproliferation. An increase in the production and/or division of lymphocytes.

Mammal. This term includes both human and non-human mammals. Similarly, the term "subject" includes both human and veterinary subjects.

Monocyte. A large white blood cell in the blood that ingests microbes or other cells and foreign particles. When a monocyte passes out of the bloodstream and enters tissues, it develops into a macrophage.

Muscle cell. A cell of striated, cardiac, or smooth muscle tissue. In striated (skeletal) muscle, a muscle cell is composed of a syncytium formed by the fusion of embryonic myoblasts. In smooth muscle, a muscle cell is a single cell characterized by large amounts of actin and myosin and capable of contracting to a small fraction of its overall length. In cardiac muscle, the muscle cell is linked to neighboring cells by specialized junctions called intercalated discs.

Pharmaceutically acceptable carriers. The pharmaceutically acceptable carriers useful are conventional. *Remington's Pharmaceutical Sciences*, by E. W. Martin, Mack Publishing Co., Easton, Pa., 15th Edition (1975), describes compositions and formulations suitable for pharmaceutical delivery of the blue-green algae and extracts described herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasticity. The capability to be molded, often used to refer to the glexibility and reversibility of tissue and lineage specification Platelets. Small cell fragments in blood derived from megacaryocytes. Platelets participate in wound healing, blood clotting, repair of damaged blood vessels and pathological inflammatory processes.

Progenitor cell. A cell that gives rise to progeny in a defined cell lineage. A "hematopoietic progenitor cell" is a cell that gives rise to cells of the hematopoietic lineage.

P-selectin. A member of the selectin family calcium-dependent lectins, also known as CD62P. P-selectin is expressed on the surface of endothelial cells, platelets (increased amounts with activation), and megacaryocytes. P-selectin can mediate binding of activated platelets to leukocytes, and can further contribute to subsequent binding of these leukocytes to endothelium. P-selectin expression on bone marrow endothelium plays a role for stem cell locations in vivo, including bone marrow retention, mobilization and homing (Frenette and Weiss, *Blood* 96(7): 2460, 2000).

Recruitment of a stem cell. A process whereby a stem cell in the circulatory system migrates into a tissue or organ. Recruitment may be facilitated by a compound or molecule, such as a chemoattractant signal or cell receptor. For example, both CXCR4 and SDF-1 have identified roles in stem cell homing. Hidalgo et. al., *Exp. Hematol.* 29(3):345-55, 2001; Kollet et al., *Blood* 97(10)3283-91, 2001.

Satellite cell. A muscle-specific stem cell, often located in the periphery of muscle tissue, and capable of migrating into a muscle to aid in tissue repair and reconstruction.

Selectin. A family of calcium-dependent lectins, also known as CD62. The three members of this family include L-selectin (CD62L), P-selectin (CD62P), and E-selectin (CD62E). These adhesion molecules are involved in slowing circulating leukocytes during their transit in venules, and are also involved in a host of other adhesive interactions, including but limited to platelet-leukocyte interactions, cell retention in certain tissues including bone marrow, and adhesion of leukocytes to inflamed endothelium.

Stem cell. A pluripotent cell that gives rise to progeny of many tissue types, including (but not limited to) the entire hematopoietic and marrow stromal cell lineages. A typical stem cell resides in the bone marrow, either as an adherent stromal cell type, or as a more differentiated cell that expresses CD34, either on the cell surface or in a manner where the cell is negative for cell surface CD34. Stem cells can also express CD133. Thus a stem cell can be a CD34+ cell, a CD133+ cell, or can be shown to express both CD34 and CD133 (see He et al., *Stem Cells and Development* 14(2): 188-198, 2005). Alternatively, a stem cell can be a cell that can be measured by fluorescently labeled aminoacetaldehyde, formed when an enzyme in stem cell cytoplasm, converts a non-fluorescent substrate into a fluorescent compound that is retained inside the stem cell and allowing its detection based on enzymatic function.

A subset of $CD34^+$ cells in bone marrow, leukapheresis products and cord blood with primitive phenotypic characteristics express CD133, a 5-transmembrane molecule of unknown function. Antibodies specific for CD133 stain 35-75% of the $CD34^+$ population depending on the source of stem cells (De Wynter et al., *Stem Cells* 16:387-396, 1998).

Transplantation of an isolated CD133+CD34+ non-adherent stem cell fraction into immunodeficient NOD/SCID mice induced high myeloid and lymphoid multilineage engraftment, suggesting that these cells are highly enriched in SCID-repopulating cells (Kuci et al. *Blood* 101:869-876, 2003).

"Totipotent" stem cells, such as hematopoietic stem cells or neuronal stem cells, generally give rise to progeny of a limited number of tissue types. Hematopoietic stem cells, muscle stem cells and neuronal precursor cells are several examples of totipotent stem cells.

Subject. An animal that has a circulatory system, including vertebrates such as humans and other veterinary subjects, such as, but not limited to, primates, canines, felines, bovines, and rodents.

Trafficking. The processes of movement of a cell from the tissue of origin and traveling within the circulatory system. In one embodiment, trafficking includes movement of a cell from the tissue of origin, homing by adhesion to the endothelium, transmigration, and final migration within the target organ. In one embodiment, tracking is the process of movement of a cell of the immune system. In another embodiment, trafficking includes stem cell mobilization. One specific, non-limiting example of trafficking is the movement of a stem cell to a target organ. Another specific, non-limiting example of trafficking is the movement of a B cell or a pre-B cell leaving the bone marrow and moving to a target organ.

Transdifferentiation. The change of a cell or tissue from one differentiated state to another, or the differentiation of a tissue-specific stem cell into another type of cell as, for example, a bone marrow stem cell differentiating into a neuron.

Transplantation. The transfer of a cell population, tissue or an organ, or a portion thereof, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or a portion thereof from one location to another in the same individual, or transplantation of a tissue or a portion thereof from one individual to another, wherein the two individuals are genetically identical.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Selectin Ligand Isolated from Blue-Green Algae Cells

Disclosed herein is an aqueous extract of blue-green algae, such as *Aphanizomenon flos aquae* (AFA), that is enriched for a selectin ligand, such as an L-selectin ligand. In one embodiment, the extract is "Extract A," an aqueous extract that includes polar compounds rapidly dissolved in water or saline, which is enriched for a selectin ligand, such as an L-selectin ligand. In another embodiment, this extract is dried using a known process, and re-suspended in an aqueous solution.

Blue-Green Algae, such as *Aphanizomenon flos aquae* (AFA) or *Spirulina* can be fractionated. Process for growing, harvesting, and concentrating blue-green algae cells have been described. Blue-green algae, such as AFA or *Spirulina*, can be isolated from any source. The source can be a natural source of blue-green algae, such as a lake (for example Klamath Lake). The source can also be a man-made source of blue-green algae such as an artificial lake or water source. The source can be an environment produced to grow and harvest blue-green algae commercially.

The blue-green algae can be used directly, or can be stored as liquid, frozen liquid, freeze-dried, or dried using the method described below. In one embodiment, the blue-green algae are harvested and dried using REFRACTANCE WINDOW™ Technology. The term "REFRACTANCE WINDOW™ Technology" refers to a system wherein the dryer utilizes the very properties of water to drive water out of the product. In brief, when water is placed over a heating source, heat gets dispersed in the water through convection. As it absorbs heat, water transmits infrared energy to the outside in three ways: evaporation, conduction, and radiation. If the surface of the water surface is covered by a transparent medium such as plastic, evaporation and its associated heat loss are blocked and only conduction occurs. The plastic membrane acts like a mirror reflecting infrared energy. When a moist material, such as wet blue-green algae is placed on the plastic surface, the water in the material creates a "window" that allows for the passage of infrared energy. It is believed that in this system the water in the material allows for radiation, conduction and evaporation all to occur, providing for exceptionally effective heat transfer. However after a few minutes, as the material dries, the infrared "window" closes and conduction remains the only means of heat transfer. Since plastic is a poor heat conductor, little heat is lost and transferred to the product. Therefore, when dried with REFRACTANCE WINDOW™ Technology, algae are exposed to heat only briefly.

In this drying system, liquid algae (cells suspended in solution) are placed on the surface of the dryer's conveyor belt. The belt is a food grade mylar (transparent polyester film) set on the surface of hot water. Heat from the circulating water is conducted to the belt and then into the water present in the product to be dried, gently speeding the natural process of evaporation while protecting natural nutrients. As the product dries and water evaporates, heat ceases to be transmitted to the product. Without being bound by theory, this prevents the degradation of polypeptides, nucleic acids, nutrients and pigments. Thus, the drying process maintains algae temperature far below the temperature of the circulating water beneath the conveyor belt.

Other drying systems can be used to produce dried algae. Generally, two factors play a role in the degradation of algae:

degree of heat and exposure time to heat. Applying a high amount of heat for a short period of time results in less degradation of the components of the blue-green algae. In one example, heat, such as a temperature of about 65° C. to about 80° C. is applied, such as a temperature of about 70° C. to about 75° C., or about 72° C. The heat can be applied for a sufficient amount of time to dry the algae, such as about 1 to about 15 minutes, or for about 2 to about 10 minutes, or for about 3 to about 7 minutes. In one example, heat is applied to the algae at 72° C. for only 3 to 5 minutes. This process is known to one of skill in the art, and is fully described at the Rossha Enterprises Website, and is described in Abonyi et al., "Evaluation of Energy Efficiency and Quality Retention for the REFRACTANCE WINDOW™ Drying System: Research Report," Washington State University, Pullman, Wash., Dec. 30, 1999). However, freeze dried cells can also be utilized.

As disclosed herein, an aqueous extract can be prepared from fresh, dehydrated, or preserved blue-green algae cells, such as *Aphanizomenon flos aquae* (AFA). The algae can be extracted with water or a suitable buffered salt solution. For example, water or buffered solutions, general of a neutral pH (about pH 7.0 to about pH 7.8, such as about pH 7.2 to about pH 7.6, or about pH 7.4) is utilized. Suitable buffered salt solutions are well known in the art and include phosphate buffered saline (such as about 0.1 M phosphate buffered saline) and commercially available culture media. The aqueous extraction is generally performed below room temperature (generally 25° C.), such as at temperatures of about 3° C. to about 15° C., such as at about 4° C. to about 10° C., or at about 4° C., but the extraction can also be performed at room temperature (about 25° C.).

In one example, one gram of dried algal material, such as dried *Aphanizomenon flos aquae* (AFA), is suspended in about 10 ml to about 50 ml, such as about 40 ml of phosphate-buffered saline (for example, 0.1 M phosphate buffered saline, pH. 7.4), and incubated at 4° C. This incubation can last for 5 minutes, half an hour, several hours, or overnight. In several examples, the algae is incubated in an aqueous solution for about half an hour to about two hours, about half an hour to about three hours, or about half an hour to about 12 hours. The algae suspended in the buffered salt solution can be protected from light to decrease degradation. Following incubation in an aqueous solution, the solid material is separated from the aqueous extract. The mixture of algae in the aqueous solution, such as the salt solution, can be mixed by repeated inversion of the vial, and centrifuged to remove solid material. For example, the suspension can be centrifuged at 400 g for 10 minutes.

Following separation of the solid material, the supernatant, which generally appears blue in color, is isolated. This extract is termed "Extract A." This supernatant optionally can be sterilized, such as by filtration. In one example, a bright blue supernatant is decanted following centrifugation and sterile filtered using a 0.22 mm filter. This filtrate can be stored, such as at about 4° C. in the dark.

The extract that contains the selectin ligand, such as the L-selectin ligand, such as Extract A, can be dried, as described above. In one example, heat, such as a temperature of about 65° C. to about 80° C. is applied to the aqueous extract, such as a temperature of about 70° C. to about 75° C., or about 72° C. The heat can be applied for a sufficient amount of time to dry the extract, such as about 1 to about 15 minutes, or for about 2 to about 10 minutes, or for about 3 to about 7 minutes. In one example, heat is applied to the extract at 72° C. for only 3 to 5 minutes. This process is similar to the process for drying algae (see Abonyi et al., "Evaluation of Energy Efficiency and Quality Retention for the REFRACTANCE WINDOW™ Drying System: Research Report," Washington State University, Pullman, Wash., Dec. 30, 1999). One of skill in the art can readily produce a dried product from an aqueous extract using known methodologies.

In several specific, non-limiting, examples an effective amount of the selectin-containing extract of blue-green algae, such as an aqueous extracted enriched for an L-selectin ligand, is from about 0.25 gram to about 5 gram, or from about 0.5 gram to about 5 gram, or from about 1 gram to about 2 gram of a dried aqueous extract, such as extract A. In one specific, non-limiting example, the effective amount of selectin-containing extract of blue-green algae is about 1 gram of a dried aqueous extract, such as extract A.

A selectin ligand can be further purified from the aqueous extract A. For example, the selectin ligand is isolated using affinity purification. In one example, Extract A is contacted with a solid substrate including L-selectin, P-selectin, or E-selectin. Magnetic beads covalently bound to a selectin, such as human L-selectin can be utilized. An exemplary amino acid sequence of human L-selectin is set forth as GENBANK Accession No. NP_000646; an exemplary amino acid sequence of murine L-selectin is set forth as CAB55488 and an exemplary sequence of mouse L-selectin is set forth as GENBANK Accession No. AAH52681. All of these sequences were available on the internet on Jun. 24, 2005, and are incorporated by reference herein. Additional exemplary sequences of L-, P-, and E-selectins can be found in the GENBANK database.

The selectin can be a native molecule, such as a human L-selectin, a human P-selectin, a murine L-selectin, or a murine P-selectin. The selectin can also be a genetically engineered form, such as a recombinant molecule that is a stable form of the L-selectin, and/or a molecule that includes a fragment of a selectin, such as the extracellular portion of the human L-selectin molecule. In one example, the selectin is a fusion protein in which the extracellular portion of human L-selectin and the Fc portion of immunoglobulin. Such recombinant fusion proteins are commercially available, such as from, for example, R&D Systems, and can be ordered through the internet. The solid substrate covalently bound to the selectin, such as, but not limited to, L-selectin, is incubated with the supernatant "Extract A" (the water-soluble extract of the blue green algae).

The material from the algae that specifically binds a selectin is then isolated. For example, the selectin ligand can cleaved from the recombinant selectin molecule using an acid treatment. The selectin ligand can also be cleaved from the recombinant selectin molecule using an alkaline treatment and/or using heat treatment.

As disclosed herein, the isolated selectin ligand has a molecular weight of about 50 kDa to about 60 kDa, such as about 55 kDa, under reducing conditions. In one example, the isolated selectin ligand has a molecular weight of about 54 kDa or about 57 kDa under reducing conditions. In one embodiment, the selectin ligand does not form a complex. For example, the selectin ligand can not form a complex with itself or with another selectin ligand.

In several examples, under non-reducing conditions, the selectin ligand can associate into a complex. Thus, if a complex of three 54 kDa subunits is formed under non-reducing conditions the molecular weight is about 162 kDa, and if a complex of three 57 kDa subunits is formed the apparent molecular weight under non-reducing conditions is about 171 kDa. If a complex of three 54 kDa subunits and three 57 kDa subunits is formed under non-reducing conditions the molecular weight of the complex is about 233 kDa. Thus, the purified selectin ligand can have a molecular weight of about 200 kDa under non-reducing conditions. If a complex of one of each ligand is formed, then the apparent molecular weight of the complex is approximately about 111 kDa. Alternatively, the two subunits can not be in a complex, and the apparent molecular weight under non-reducing conditions will be the same as under reducing conditions. The selectin ligand can be a protein or a glycoprotein.

The extracts and compositions disclosed herein can be administered in any form, including as solids such as tablets or powders or as a liquid preparation. In one example, the compositions are formulated for enteral administration. An example of a formulation of use is a pharmaceutical preparation (such as a tablet, enteral liquid, parenteral liquid, capsule, intranasal liquid or other form). In a particular disclosed example the composition is a pharmaceutical preparation, in particular a tablet or capsule. As is known in the art, compositions suitable for oral administration may be presented as discrete units such as capsules, cachets, or tablets, each containing a therapeutically effective amount of the composition, as a powder or granules, or as a solution or a suspension in an aqueous liquid. Thus, dosage forms include tablets, capsules, dispersions, suspensions, solutions, capsules and the like. Because of their ease of administration, tablets and capsules represent a convenient oral dosage unit form, in which case solid pharmaceutical carriers as described above are employed. However, the compounds can also be administered by controlled release means, or can be formulated for other means of delivery, such as, but not limited to intranasal or transdermal delivery.

The compositions can include inactive ingredients such as binding agents (such as pregelatinized maize starch, polyvinylpyrrolidone or hydroxypropyl methylcellulose); binders or fillers (such as lactose, pentosan, microcrystalline cellulose or calcium hydrogen phosphate); lubricants (such as magnesium stearate, talc or silica); disintegrants (such as potato starch or sodium starch glycolate); or wetting agents (such as sodium lauryl sulphate).

In one example, a tablet containing the compositions disclosed herein, such as but not limited to an extract enriched for an L-selectin ligand or a solid form thereof, or a purified selectin ligand, can be prepared by compression or molding, optionally, with one more accessory ingredients. Compressed tablets can be prepared by compressing in a suitable machine, a free-flowing form such as powder or granules of a dried extract and/or selectin ligand, optionally mixed with a binder, lubricant, inert diluent, surface active or dispersing agent. The composition, such as the tablet, can include pharmaceutically acceptable components such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like. The tablets or capsules can be coated by methods well known in the art.

Liquid preparations for oral administration can take the form of, for example, solutions, syrups or suspensions, or they can be presented as a dry product for constitution with water or other suitable vehicle before use (see the examples section). Such liquid preparations can be prepared by conventional means with pharmaceutically acceptable additives that are inactive agents, such as suspending agents (such as sorbitol syrup, cellulose derivatives or hydrogenated edible fats), emulsifying agents (such as lecithin or acacia), and preservatives (such as methyl or propyl-p-hydroxybenzoates or sorbic acid). The compositions can also be made to be pleasant tasting, and thus can contain buffer salts, flavoring, coloring and sweetening agents as appropriate.

Diluents and other inactive ingredients such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed. The composition can also include a sweetener, such as a natural (for example, sugar or honey) or artificial sweetener (for example, saccharine), if desired. Generally, the carriers, sugars, diluents, stabilizers, buffers, flavoring and texturing ingredients are considered to be inactive ingredients, as they do not impart a therapeutic effect in and of themselves.

In several embodiments, the composition can include one or more additional extract(s) of *Aphanizomenon flos aquae* (AFA) that induces the migration of stem cells. This extract can be obtained by extracting liquid *Aphanizomenon flos aquae* (AFA) in an alcohol, such as but not limited to, ethanol or methanol. In one example, the additional extract is produced by extracting *Aphanizomenon flos aquae* (AFA) in about 10% to about 20% ethanol. In one example, the composition includes an extract prepared by extracting liquid *Aphanizomenon flos aquae* (AFA) in about 10% ethanol. In one example, the additional extract is produced by incubating liquid AFA in about 10% ethanol at a temperature of about 65° C. to about 85° C. is applied to the aqueous extract, such as a temperature of about 70° C. to about 95° C., or about 85° C. The solution is then centrifuged and the supernatant is dried (see above). In one embodiment, about 50 mg to about 500 mg, such as about 100 mg to about 250 mg, such as about 150 mg of the dried product is administered to the subject.

In one example, a composition of use includes about 0.25 gram to about 5 gram, of from about 0.5 gram to about 5 gram, or from about 1 gram to about 2 gram of a dried selectin-containing extract, such as a solid form of an aqueous extract enriched for an L-selectin ligand, such as extract A. In one specific, non-limiting example, the composition includes about 1 gram of a dried selectin-containing extract of blue-green algae (such as AFA), such as a solid form of an aqueous extract enriched form an L-selectin ligand, such as extract A. The composition also includes about 150 mg of a second dried extract of AFA, wherein the second dried extract is produced by incubating AFA in about 10% to about 20% ethanol at about 70° C. to about 90° C. for about one to three hours, such as by incubating AFA in about 10% ethanol for at about 85° C. for about one to three hours.

Enhancing Stem Cell Mobilization

A method is described herein for enhancing stem cell mobilization by administering to a subject a therapeutically effective amount of an aqueous extract of a blue green algae such as *Aphanizomenon flos aquae* (AFA), enriched for a selectin ligand, such as L-selectin, and/or a therapeutically effective amount of a purified selectin-ligand. The selectin ligand can be an L-selectin, P-selectin, and/or an E-selectin ligand. Selectin ligands stimulate stem cell release (Frenette and Weiss, *Blood* 196(7): 2460, 2000). The subject can be any subject, such as a human or a veterinary subject.

An aqueous extract of blue-green algae enriched for a selectin ligand, such as an L-selectin, or a purified selectin-ligand from blue-green algae, can be administered alone or in combination with other agents. In several embodiments, the purified selectin ligand and/or the aqueous extract enriched for a selectin ligand (or a solid form thereof), is included in a pharmaceutical composition along with a pharmaceutically acceptable carrier. Therapeutically effective amounts of additional components, such as solid forms of additional extracts, can also be administered to the subject. In one embodiment, a therapeutically effective amount of a solid form of an aqueous extract of a blue green algae enriched for a selectin ligand is administered to the subject. Thus, a method is provided herein for increasing the mobilization of stem cells in a subject, comprising administering a therapeutically effective amount of an aqueous extract of blue-green algae enriched for a selectin ligand, such as L-selectin, thereby increasing the mobilization of stem cells in the subject.

In one specific, non-limiting example, the aqueous extract is dried, such that a solid form is produced, and a therapeutically effective amount of the solid form is administered to a subject of interest. The therapeutically effective amount of the extract, such as an aqueous extract of blue-green algae enriched for a selectin ligand, is from about 0.01 to about 1.0 g per kg body weight, such as about 0.05 to about 0.5 gram per kg body weight, or from about 0.1 to about 0.5 gram per kg body weight. In another specific, non-limiting, example the effective amount of the solid form of an aqueous extract of blue-green algae enriched for a selectin ligand is from about 0.25 gram to about 5 gram, of from about 0.5 gram to about 5 gram, or from about 1 gram to about 2 gram. In one specific, non-limiting example, the effective amount of the solid form of the aqueous extract of blue-green algae enriched form a selectin ligand is about 1 gram.

The active agents of the compositions disclosed herein can be admixed with a carrier. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

This effective amount may be administered at a given frequency, such as about once a week, about twice a week, about three times a week, once a day, about twice a day, about three times a day, or more. One of skill in the art can readily determine a therapeutically effective amount of a purified selectin ligand, or an aqueous extract enriched from a selectin ligand. In one specific, non-limiting example, the amount of circulating stem cells, such as the amount of cell expressing CD34, is assessed.

The therapeutically effective amount of an aqueous extract blue-green algae enriched for a selectin ligand and the frequency of administration of these compositions, can depend on a variety of factors, such as the genus or species of algae utilized, the general health of the subject being treated, and the physiological characteristics (e.g., height, weight, body fat percentage, metabolism, etc.) of the subject being treated. The aqueous extract can be administered directly, without altering the physical parameters, or can be administered in another physical form. Thus, in one embodiment, the extract is dried and is administered as a solid. In another embodiment, the aqueous extract is dried, and then a specific amount is dissolved in a carrier and subsequently administered to the subject.

Specific assays for determining a therapeutically effective amount of an aqueous extract, such as an aqueous ligand enriched for a selectin are provided herein. In one specific, non-limiting example, different amounts of a selectin ligand-containing extract of blue-green algae, such as AFA, are consumed by human subjects and the presence and/or quantity of stem cells (which can include subtypes of such cells) present in the circulatory system is detected and/or analyzed. In another embodiment, an animal (such as a mouse, rat, or other veterinary) model is utilized, and the population of newly integrated stem cells is monitored in various tissues (see the Examples below). It should be noted that the methods disclosed have equal application in medical and veterinary settings.

Regardless of how provided or administered, the blue-green algae extract and/or purified selectin ligand induce a transient increase in the population of circulating stem cells, such as CD34+ stem cells and/or CD133+ cells. The blue-green algae extract can also include a transient increase in stem cells that can be measured by fluorescently labeled aminoacetaldehyde. This procedure is described on the stem cell website. Briefly, fluorescent-labeled aminoacetaldehyde can freely diffuse into cells. An intracellular enzyme ALDH (aldehyde dehydrogenase) converts this into fluorescent-labeled aminoacetate, which cannot diffuse out of the cells. Thus, cells that have the enzyme ALDH (such as stem cells) become fluorescent. Other cells (such as cells that are not stem cells, including differentiated cells) appear non-fluorescent after washing.

Enhancement of stem cell mobilization may be measured by assaying the response of stem cells to a particular dose of blue-green algae extract. In one embodiment, providing a purified selectin-ligand from blue-green algae to a subject will enhance mobilization of that subject's stem cells within a certain time period, such as less than about 5 hours, less than about 4 hours, less than about 2 hours, less than about 1 hour, less than about 30 minutes, or less than about 10 minutes following administration.

In one embodiment, administration of the aqueous extract of blue-green algae enriched for a selectin ligand, and/or the purified selectin ligand, results in the mobilization of stem cells into the circulation from about 10 to about 30 minutes following administration. Mobilized stem cells will enter the circulatory system, thus increasing the number of circulating stem cells within the subject's body. The percentage increase in the number of circulating stem cells compared to a normal baseline may about 25%, about 50%, about 100% or greater than about 100% increase as compared to a control. In one embodiment, the control is a baseline value from the same subject. In another embodiment, the control is the number of circulating stem cells in an untreated subject, or in a subject treated with a placebo or a pharmacological carrier.

In some embodiments, the subject is healthy. In other embodiments, the subject is suffering a disease or physiological condition, such as immunosuppression, chronic illness, traumatic injury, or degenerative disease. In certain embodiments, the subject suffers a disease or condition of the skin, digestive system, nervous system, lymph system, cardiovascular system, or endocrine system. In specific embodiments, the subject suffers osteoporosis, Alzheimer's disease, cardiac infarction, Parkinson's disease, traumatic brain injury, multiple sclerosis, cirrhosis of the liver, or any of the diseases and conditions described in the Examples below.

EXAMPLES

The following examples are provided to illustrate particular features of various described embodiments. The scope of the present invention should not be limited to those features exemplified.

Example 1

Production of AFA and Extraction

A blue-green algae, *Aphanizomenon flos aquae* (AFA), was isolated from Klamath Lake. The blue-green algae was dried using REFRACTANCE WINDOW™ Technology.

One gram of dried algal material was resuspended in 10 ml phosphate-buffered saline or water and incubated 1 hour at 4° C. and protected from light. This slush was mixed by repeated inversion of the vial, and centrifuged at 400 g for 10 minutes. The bright blue supernatant was decanted and sterile filtered using a 0.22 mm filter. This filtrate was stored cold and dark, and used within the same day of preparation. This extract was called Extract A

Example 2

Selectin Ligand Extracted from AFA-W

Materials and Methods

Buffers and media: For cell cultures, cells were re-suspended and cultured in RPMI-1640 with 10% fetal calf serum, 1% penicillin and streptomycin, and L-glutamine. For immunostaining, cells were washed, resuspended, and stained in phosphate-buffered saline containing 0.02% Azide and 1% fetal calf serum or bovine serum albumin. For proliferation assays and for stimulation for phosphotyrosine blotting assays, cells were prepared in RPMI 1640 with phenol red, 10% Fetal Calf Serum (Gibco, Grand Island N.Y.), 1% glutamine, 1% Penicillin and 1% Streptomycin.

Cyanobacterial extracts: Dried powder of the freshwater blue-green algae *Aphanizomenon flos aquae* (AFA) was obtained from Upper Klamath Lake in Oregon, USA. For early experiments, a freeze-dried powder was used. For later experiments, a powder was obtained from Desert Lake Technologies LLC, Keno, Oreg., which had been dried using the REFRACTANCE WINDOW™ drying technology. Dried powder of *Spirulina platensis* was obtained from Healthforce Nutritionals Inc, Escondido Calif. One gram of dried algal material was resuspended in 10 ml phosphate-buffered saline, and incubated overnight at 4° C. and protected from light. The slush was mixed by repeated inversion of the vial, and centrifuged at 400 g for 10 minutes. The bright blue supernatant was decanted and sterile filtered using a 0.22 mm filter. This filtrate was stored cold and dark, and used within the same day of preparation.

Monoclonal antibodies: The CD62L monoclonal antibody TQ1 (specific for the ligand-binding area of the L-selectin molecule) linked to phycoerythrin (PE), was purchased from Coulter (Hialeah, Fla.). CD45-PerCP, CD11b-PE, CD14-PE, and isotype control antibodies were obtained from Becton-Dickinson.

Capturing of ligand using Dynabeads and chimera proteins: In order to identify the molecular weight of the selectin binding compound, a cell-free method was used, in which Dynabeads (Dynal Biotech Inc., Lake Success, N.Y.) coated with Protein G were incubated with a selectin chimera protein (R & D Systems Inc., Minneapolis, Minn.). The chimera protein is a fusion of the extracellular domain of human L-selectin, P-selectin, or E-selectin, with the Fc portion of human immunoglobulin G. The chimera protein was covalently linked onto the Protein G-coated Dynabeads using the protocol recommended by the manufacturer, in which beads were incubated for 1 hour in a freshly made 5.4 mg/ml solution of dimethyl pimelimidate×2HCl (Sigma Aldrich) in 0.2 M triethanolamine buffer pH 8.0 (Sigma Aldrich). The cross-linking was stopped by removing the beads from the cross-linking solution, and resuspending in 50 mM TRIS buffer pH 7.5 (Sigma Aldrich) for 15 minutes. Unbound chimera was eluted off the beads by two washes in citrate/citric acid buffer pH 2.8. The beads were then washed several times in PBS pH 7.4, and added to a freshly made AFA water extract. Bound material from the AFA water extract was eluted in one of three ways: 1) by boiling in Laemmli buffer containing beta-mercaptoethanol, 2) eluting with pH 12.5, and 3) competition for the selectin ligand binding site using known selectin ligands. It was found that a compound of apparently identical molecular weight was affinity purified by both L-selectin and P-selectin.

In parallel experiments, beads coated with recombinant human L-selectin/IgG1 fusion protein were used to see whether a similar water extract from other blue-green algae, *Spirulina platensis*, contained a similar selectin-binding compound.

Electrophoresis: Samples of eluant from the Dynabead affinity method were prepared for gel electrophoresis by mixing 1:1 v/v in Laemmli sample buffer (Biorad cat# 161-0737) with mercaptoethanol. SDS gel electrophoresis was performed on 4-15% gels (BioRad) in TRIS/glycine/SDS buffer (Biorad cat# 161-0732) for 1 hour at 120 V.

Electrophoresis for native protein was performed with SDS-free reagents, using Native Sample Buffer (Biorad cat# 161-0738) for loading, and TRIS/glycine buffer (Biorad cat# 161-0734) for electrophoresis.

Human subjects: Healthy human volunteers were recruited upon informed consent from laboratory staff and students between 20 and 45 years of age. Blood samples were obtained by venopuncture under aseptic conditions, and processed immediately.

Isolation of Peripheral Blood Mononuclear Cells (PBMC): Peripheral venous blood was layered onto Ficoll-Hypaque (Amersham), and centrifuged for 25 minutes at 400 g. The PBMC-rich interface was harvested, and the cells washed twice in RPMI.

Isolation of Polymorph Nucleated Cells (PMN): Peripheral venous blood was mixed with dextran70 in 0.9% saline to a final concentration of 1% dextran at room temperature. Sedimentation was allowed for 1 hour. The leukocyte-rich supernatant was harvested and the leukocytes pelleted by centrifugation. The pellet was resuspended in 2 ml of phosphate buffered saline which was then layered on top of 3 ml Ficoll-Hypaque, and gradient centrifugation performed to separate mononuclear cells (lymphocytes and monocytes) from neutrophils. The pellet containing neutrophils was resuspended in saline. Cells were washed, resuspended in a nutrient-rich medium (RPMI 1640), and kept on ice until use.

Immunostaining for L-selectin: Fresh and formalin-fixed peripheral blood leukocytes were distributed into wells in a V-bottom 96-well microtiter plate at the approximate concentration of $10^5$ cells per well. A freshly prepared water-based extract of the blue-green algae AFA was prepared in physiological saline and serial dilutions performed. Cells were resuspended in either PBS, PBS-AFA-W, PBS-AFA-W-azide, or PBS-PC at various dilutions. Cells were incubated at room temperature and in the dark for 20 minutes. The unfixed fraction was not in contact with sodium azide during treatment with AFA extract, but was resuspended in sodium azide-containing buffer for subsequent immunostaining. This was to allow for free cytoskeletal movements and shedding of L-selectin. The fraction that was kept in 0.02% sodium azide was in contact with sodium azide during the whole procedure, both treatment with AFA extract and subsequent immunostaining. This would block cytoskeletal movement and reduce or block L-selectin shedding. After incubation with or without AFA-W, buffer was added, and cells centrifuged. Supernatant was discarded, and cells resuspended in a volume of 50 µl phosphate-buffered saline containing 1% fetal calf serum and 0.05% azide. Optimal amounts of monoclonal antibodies, as determined by previous titrations, were added. Plates were incubated at room temperature for 10 minutes, buffer was added, and plates centrifuged. Supernatants were discarded, cells resuspended in 50 µl buffer, and fixed in 1% formalin. Samples were kept cold and dark until acquisition by flow cytometry. Acquisition was performed within 24 hours of fixation.

Immunostaining for CXCR4 expression induced by L-selectin ligands: The binding of Fucoidan to L-selectin results in externalization of pre-made CXCR4 onto the cell surface, followed by internalization, creating a window in time for responsiveness to chemotactic factors. This system was used to examine whether AFA-W would compete with Fucoidan for binding to L-selectin on the leukocyte cell surface, and to assess whether it would block this functional effect from another L-selectin ligand. To do so, freshly purified human PBMC were resuspended in RPMI, and distributed in a series of round-bottom microwells. Fucoidan was added to one series of wells, AFA-W to another series, and a mixture of Fucoidan and AFA-W was added to the third series of wells. At different time points (1, 10, 20, 30, 40, 60 minutes), PBS containing sodium azide was added to wells in order to stop cytoskeletal movements, and thereby stop the recycling of CXCR4, allowing staining for CXCR4 expressed at the cell surface at each time point. Cells were washed in phosphate-buffered saline containing azide, stained with CXCR4-PE using the staining protocol described above, fixed in formalin, and analyzed by flow cytometry.

Estimation of molecular weight of native versus denatured components of the selectin ligand from AFA: The distances on the gel were measured for the known molecular weight markers. The position of the AFA-derived selectin ligand (double band) was plotted onto that graph.

Example 3

Stem Cells are Mobilized by an Aqueous Extract from AFA

This experiments described below demonstrates that an aqueous extract of AFA (Extract A, also termed "AFA-W") is enriched for a selectin ligand and can be used to enhance mobilization of CD34+ stem cells.

Healthy human volunteers were identified, and the proportion of CD34+ cells was evaluated in the peripheral blood (circulating CD34+ cells) of each person prior to consumption of the selectin-containing extract of blue-green algae as well as 10 minutes, 30 minutes, 60 minutes, and 120 minutes after consumption. The volunteers were instructed to limit physical and mental activity for a time before and after consumption of the AFA extract.

In one embodiment, 5 grams of dried AFA was extracted in 40 ml of water and the participant drank the water. In another embodiment, participants consumed 750 mg of dried L-selectin-ligand containing extract of AFA. Red blood cells in whole blood samples obtained from each volunteer were lysed using FACS lysing solution (Beckton-Dickinson, San Jose, Calif.). The remaining cells were washed and stained with monoclonal antibody HPCA-2 conjugated with fluorescein isothiocyanate. Samples were fixed in 1% formalin and analyzed by flow cytometry using a FacsCalibur flow cytometer (Becton-Dickinson, San Jose, Calif.) and CellQuest software (Becton-Dickinson, San Jose, Calif.).

FIG. 1 illustrates that consumption of the selectin-ligand containing extract of AFA triggered a transient increase in circulating stem cells. Specifically, the X-axis shows the time course of a typical experiment at 0, 10, 30, and 60 minutes after ingestion of the L-selectin-ligand containing extract of AFA, expressed as a percentage of the control level. At the time of ingestion, the proportion of circulating CD34+ cells is the same as the control. The peak increase in circulating CD34+ cells was observed at about 10-30 minutes after consumption. At this time point, the number of circulating CD34+ cells was increased 2-fold (greater that 200%) over the control value. By 1 hour after ingestion of the selectin-ligand containing extract of AFA, the circulating CD34+ cells had returned to the baseline value. Therefore, an aqueous extract of AFA can enhance the release of endogenous stem cells (e.g. CD34+ cells) from bone marrow and other anatomical sites into circulation. Consumption of the selectin-ligand containing extract of AFA mobilizes CD34+ stem cells.

Example 4

An Aqueous Extract of AFA Contains a Selectin Ligand

The experiments described below document that AFA contains a water-soluble compound that specifically reduces TQ1 immunostaining of L-selectin on human lymphocytes, monocytes, and neutrophils.

Peripheral Blood Mononuclear Cells (PBMC) were isolated by layering peripheral venous blood onto Ficoll-Hypaque (Amersham), and centrifuged for 25 minutes at 400 g. The PBMC-rich interface was harvested, and the cells washed twice in RPMI. Polymorphonuclear Cells (PMN) were isolated by mixing peripheral venous blood with dextran70 in 0.9% saline to a final concentration of 1% dextran at room temperature. Sedimentation was allowed for 1 hour. The leukocyte-rich supernatant was harvested and the leukocytes pelleted by centrifugation. The pellet was resuspended in 2 ml of phosphate buffered saline which was then layered on top of 3 ml Ficoll-Hypaque, and gradient centrifugation performed to separate mononuclear cells (lymphocytes and monocytes) from neutrophils. The pellet containing neutrophils was resuspended in saline. Cells were washed, resuspended in a nutrient-rich medium (RPMI 1640), and kept on ice until use.

Fresh and formalin-fixed peripheral blood leukocytes were distributed into wells in a V-bottom 96-well microtiter plate at the approximate concentration of $10^5$ cells per well. A freshly prepared water-based extract of the blue-green algae AFA was prepared in physiological saline and serial dilutions performed. Cells were resuspended in either PBS, PBS-AFA-W, PBS-AFA-W-azide, or PBS-PC at various dilutions. Cells were incubated at room temperature and in the dark for 20 minutes. The unfixed fraction was not in contact with sodium azide during treatment with AFA extract, but was resuspended in sodium azide-containing buffer for subsequent immunostaining. This was to allow for free cytoskeletal movements and shedding of L-selectin. The fraction that was kept in 0.02% sodium azide was in contact with sodium azide during the whole procedure, both treatment with AFA extract and subsequent immunostaining. Sodium azide blocks cytoskeletal movement and reduces or blocks L-selectin shedding. Therefore, any reduction in staining for L-selectin with a monoclonal antibody is due to direct competition with a compound in AFA Extract.

After incubation with or without Extract A (AFA-W) buffer was added, and cells centrifuged. Supernatant was discarded, and cells resuspended in a volume of 50 µl phosphate-buffered saline containing 1% fetal calf serum and 0.05% azide. Optimal amounts of monoclonal antibodies, as determined by previous titrations, were added. Plates were incubated at room temperature for 10 minutes, buffer was added, and plates centrifuged. Supernatants were discarded, cells resuspended in 50 µl buffer, and fixed in 1% formalin. Samples were kept cold and dark until acquisition by flow cytometry. Acquisition was performed within 24 hours of fixation. The CD62L monoclonal antibody TQ1 (specific for the ligand-binding area of the L-selectin molecule) linked to phycoerythrin (PE), was purchased from Coulter (Hialeah Fla.).

The incubation of PBMC and PMN with the water extract from AFA (AFA-W) resulted in reduction of immunostaining with the TQ1 anti-human L-selectin monoclonal antibody, which is known to be specific for the ligand-binding area of L-selectin (Spertini et al., $J$ $Immunol.$ 147(3):942-9, 1991). The AFA-W mediated reduction of TQ1 staining was strongest on lymphocytes and PMN, but was also observed on monocytes (FIG. 2A). On lymphocytes and PMN, an approximate 40-70 fold reduction in TQ1 staining was seen when cells were pre-incubated with AFA-W, in contrast to a 15-fold reduction for monocytes.

Figure 2:
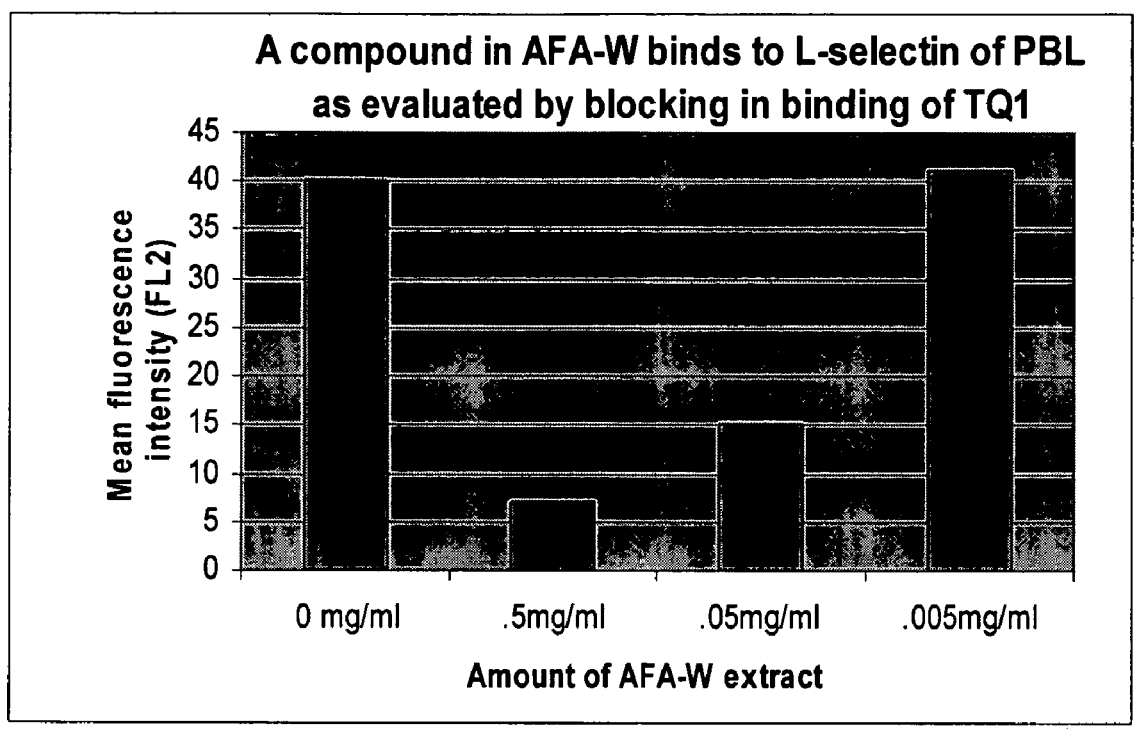
FIG. 2 is a bar graph showing flow cytometry that was performed on human lymphocytes, monoclytes, and polymorph nucleated cells, where the monoclonal antibody TQ1, specific for the ligand-binding area of human L-selectin, was used to demonstrate that AFA extract A contains a compound that competes for binding on the L-selectin ligand-binding site. The effect of competition between the TQ1 antibody and the compound from AFA Extract A is concentration-dependent.

The expression of CD11b was slightly up-regulated, while no significant changes were observed for other adhesion markers (CD11a, CD18, CD29, CD49d, CD49e, and CD44). Formalin-fixed peripheral blood lymphocytes were incubated in the absence or presence of serial dilutions of AFA-W. Staining of lymphocytes with the TQ1 antibody showed a dose-dependent reduction in TQ1 binding to L-selectin with increasing concentrations of Extract A. As the effect was seen also on the formalin-fixed lymphocytes, the reduced staining could not be due to shedding of L-selectin. (FIG. 2).

Example 5

Figure 3:
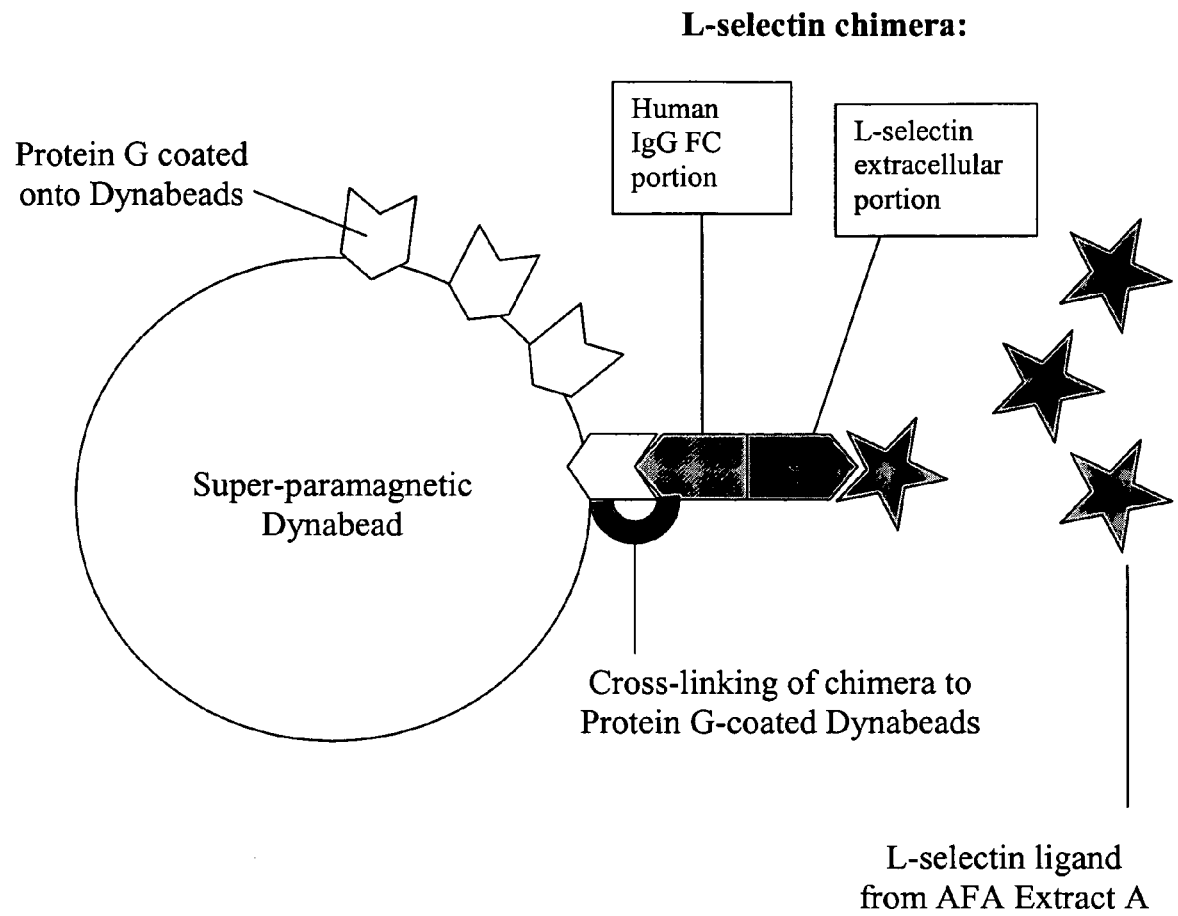
FIG. 3 is a schematic illustration of the method used to purify the selectin ligand from AFA Extract A. Magnetic beads were coated with Protein G, which binds the Fc portion of immunoglobulin. These beads were used to capture a chimerical recombinant protein consisting of the extracellular portion of human L-selectin, joined together with the Fc portion of human immunoglobulin IgG1. A chemical reaction was performed to form covalent bindings between the Fc portion of the chimera and the Protein G on the magnetic beads. These beads, now coated with the chimera, with the extracellular portion of human L-selectin reaching out from the beads, were used to capture the ligand for L-selectin in AFA extracts.

AFA Selectin Ligand Blocks the Expression of Chemokine Receptors Triggered by Fucoidan in the KG-1a CD34$^{bright}$ Cell Line The primitive cell line KG-1a is brightly positive for CD34 and for L-selectin, as evaluated by staining with the TQ1 monoclonal antibody. KG-1a also contains intracellular reservoirs of the CXCR4 chemokine receptor that are externalized upon L-selectin ligation. Incubation of KG-1a with the Fucoidan, an L-selectin agonist, triggers the expression of the chemokine receptor CXCR4. AFA Extract A blocked the Fucoidan-mediated effect on CXCR4 expression (FIG. 3).

Example 6

Purification of the L-Selectin Ligand from AFA

Figure 4A:
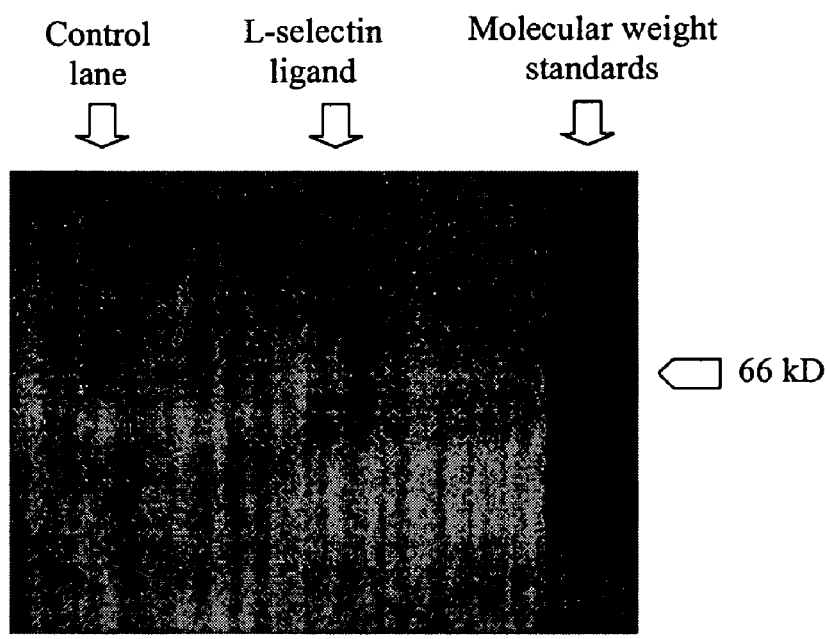
FIGS. 4A-4B are digital images that show gel electrophoresis that illustrates the approximate molecular weight of the compound that was affinity purified from AFA extract A, when the affinity method described in FIG. 3 was employed. The figures are digital images of gels, wherein gel electrophoresis was performed on material eluted off the magnetic beads after these beads had captured the selectin ligand from AFA Extract A.

A selectin ligand was isolated from AFA using magnetic beads covalently bound to genetically engineered fusion protein in which the extracellular portion of human recombinant L-selectin or P-selectin is coupled to the Fc portion of immunoglobulin. The beads are incubated with the water-soluble fraction of AFA and the selectin ligand is isolated (see FIG. 4A: L-selectin, FIG. 4B: P-selectin). The beads were collected using a magnet and washed many times. The beads were then exposed to an acid treatment or boiling or an alkaline treatment to break the bond between the ligand and the recombinant selectin. The selectin ligand was also isolated using an affinity column.

Figure 4B:
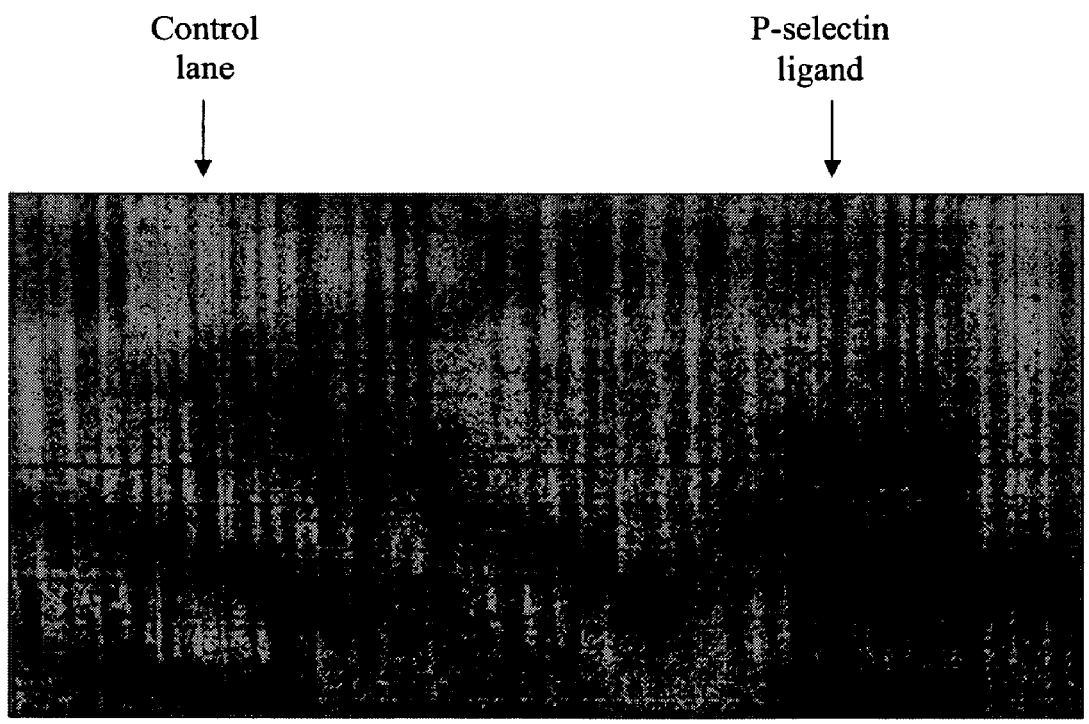

When the selectin ligand is recovered under reducing conditions, it is a dimer made of two subunits of approximately 54 kDa and 57 kDa (FIG. 4B). A composite molecule based on these subunits could have molecular weights of 108, 111, or 114 kDa approximately, and higher multiplicities thereof. Using size exclusion techniques, when the extract A fraction was passed through a 100 kDa filter, the ligand was found in higher concentrations in the fraction above 100 kDa. Therefore, the ligand can be isolated as a dimer of at least 100 kDa.

Example 7

The Selectin Ligand Extracted from AFA is not a Found in Extract B

Figure 5:
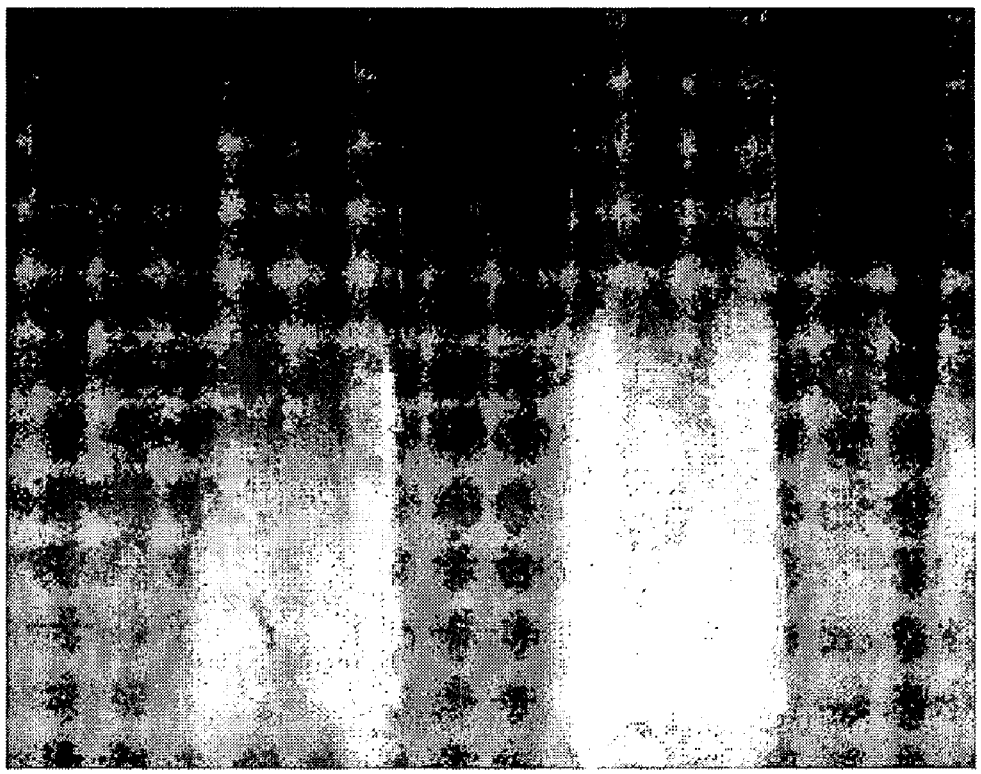
FIG. 5 is a digital image of a gel, wherein gel electrophoresis was performed on material eluted off the magnetic beads after these beads had been utilized to capture potential selectin ligands in AFA Extract A versus Extract B. The selectin ligand from AFA was found in Extract A. No selectin ligand from AFA can be detected in Extract B. Lane 1 is a negative control, Lane 2 shows the ligand purified from Extract A (arrow), and Lane 3 shows that a corresponding band was not seen in Extract B.

Extract B was produced in several steps, first by extracting compounds into ethanol, then back into a polar buffer (water, saline). The first step was to produce a yellow/brown powder from dried AFA, initially during 3 hours at 50° C. with an aqueous solution containing 20% ethanol. The supernatant was decanted and the solids were precipitated by adding ethanol to a final 80% concentration. The precipitate was dried using REFRACTANCE WINDOW™ drying technique. When this yellow powder was put back into aqueous solution (water or saline), an orange extract was produced. Solids were removed by centrifugation, and the supernatant sterile filtered. This liquid is Extract B. This extract was incubated with the coated magnetic beads described above. Extract B did not contain a selectin ligand (FIG. 5).

Example 8

Selectin Ligand from Blue-Green Algae Modulates CXCR4 Expression

Stem cells are maintained within the bone marrow environment at least in part through the selectin adhesion molecules. When selectin is engaged by an appropriate ligand, it triggers the expression of the cytokine receptor CXCR4. CXCR4 is a specific receptor for Stromal Derived Factor 1 (SDF-1) and binding of SDF-1 to CXCR4 helps to maintain stem cells bound to the bone morrow. Inhibition of selectin ligand binding reduces the expression of CXCR4, which leads to a detachment of stem cells from the bone marrow and their release in the bloodstream.

Figure 6:
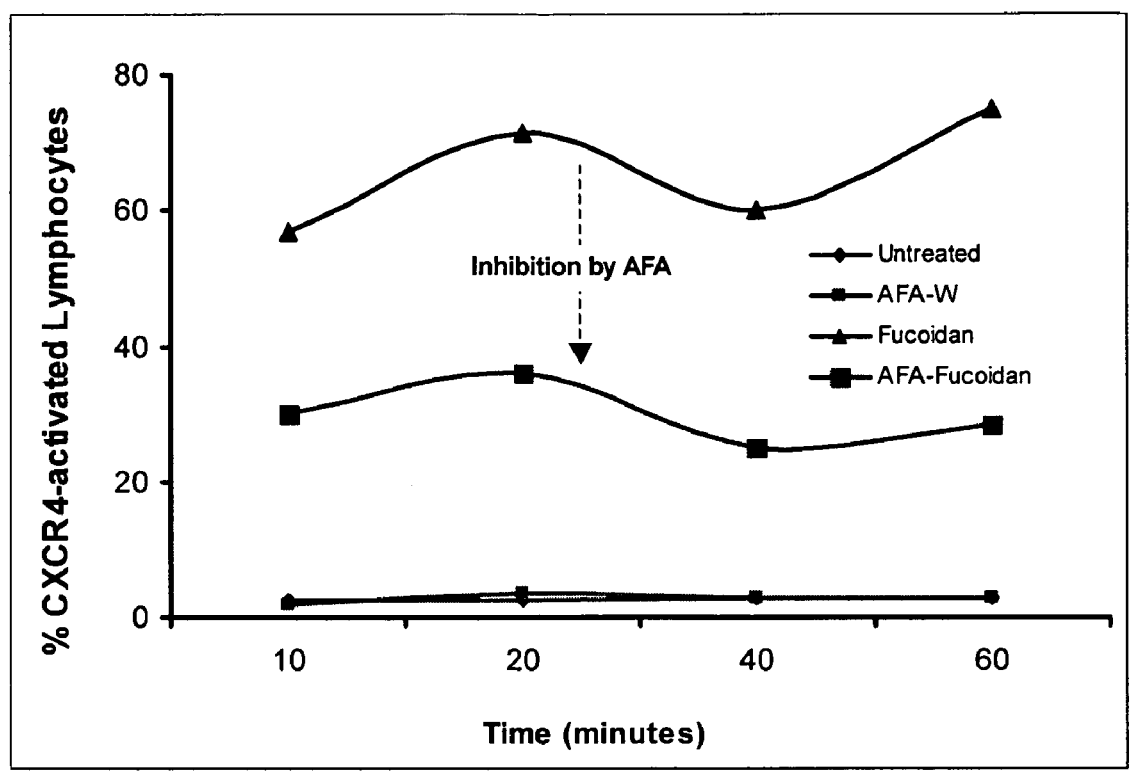
FIG. 6 is a line graph showing the results from flow cytometry analysis of the expression of the chemokine receptor CXCR4, as it is induced by a known L-selectin ligand, Fucoidan. The data indicates that the known L-selectin ligand Fucoidan, competes with the compound from AFA for binding to L-selectin on human peripheral blood lymphocytes.
Figure 7:
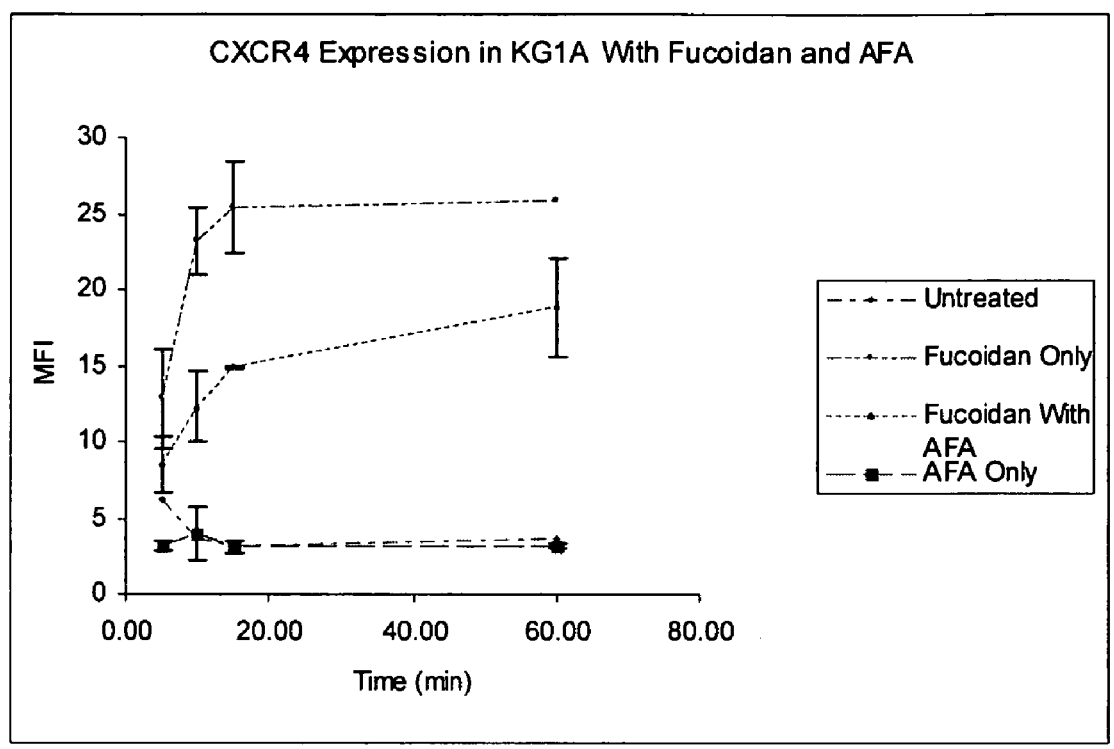

To demonstrate the physiological effect of the selectin ligand from AFA, in one embodiment the selectin ligand was tested on CXCR4 expression triggered by fucoidan, a known L-selectin ligand that stimulates CXCR4 expression. The expression of CXCR4 receptors following exposure to fucoidan was evaluated on lymphocytes using flow cytometry. Incubation with the AFA selectin ligand significantly inhibited the expression of CXCR4 on human lymphocytes (FIG. 6) and on the human CD34+ progenitor cell line KG-1a (FIG. 7), indicating that this is a mechanism by which the AFA selectin ligand can trigger stem cell mobilization.

Example 9

Stem Cells from Bone Marrow Populate Multiple Distant Tissues

A murine model can be used to evaluate the ability of stem cells mobilized by consumption of blue-green algae to populate distant tissues of the body. Male mice are selected as bone marrow donor animals, while all recipient mice are females. Female recipients are sub-lethally irradiated prior to injection of male bone marrow cells into their tail veins. Two groups of mice are evaluated. The first group of 20 animals are sub-lethally irradiated, injected with bone marrow, and put on normal feed. The second group of 20 animals is also sub-lethally irradiated, receive male bone marrow, and are fed a diet of normal feed plus 0.5 to 15% w/v of the selectin-ligand containing fraction of AFA.

About $6 \times 10^6$ nucleated cells of adult bone marrow is harvested from male mice aged 8-10 weeks and injected into the tail veins of sub-lethally irradiated isogenic adult female recipients, also aged 8-10 weeks. Mice from each group are sacrificed at each of the following time points: time 0, 1 week, 2 weeks, 3 weeks, 4 weeks, and 8 weeks. At time points 2 and 8 weeks, 6 mice are sacrificed from each group. At all other time points, 2 mice are sacrificed from each group.

During the first two weeks after injection, 15 microliters of whole blood is taken from the ear, tail, or paw, and immediately diluted in 200 microliters of buffer (phosphate buffered saline, pH=7.2, 2% serum, 0.02% azide) to dilute clotting factors and prevent coagulation. The blood samples are assayed to monitor the repopulation of platelets, red blood cells, and leukocytes within the blood. A portion of the blood sample is used for obtaining a cell count and for differential evaluation of red blood cells versus white blood cells. The sample is assayed using a flow cytometer, and the proportion of neutrophils, lymphocytes, and monocytes will be evaluated using forward and side scatter. The blood leukocytes will be examined for male origin using flow cytometry.

At time of sacrifice, various cell and tissue types will be examined for Hy antigen, which demonstrates that the cell or tissue originated in a male mouse. Brains are harvested and the entire brain is examined, including the olfactory bulb, hippocampus, cortical areas, and cerebellum. Bone marrow, heart muscle, hind leg muscle, liver, pancreas, sections of small intestine, and lung tissue are examined for presence of cells with Y chromosome, either by detection of surface Hy antigen by immunofluorescence, or by fluorescence in situ hybridization using probes for the Y chromosome. These data will document to what extent a diet containing blue-green algae promotes the homing, implantation, and differentiation process of the injected bone marrow stem cells.

Example 10

Stem Cells from Bone Marrow Populate Multiple Distant Tissues

A study similar to that described above is conducted using transgenic male mice carrying the gene for green fluorescent protein (GFP) and isogenic female mice as recipients. The animals are treated, fed, and sacrificed as described above, and blood samples are also analyzed in a similar manner.

Blood leukocytes are examined for the expression of GFP using flow cytometry and, at time of sacrifice, various cell and tissue types will be examined for GFP antigen, which demonstrates the donor origin. Tissues and organs are harvested as described above and the presence of cells carrying GFP is detected by flow cytometry or fluorescence microscopy.

Example 11

Increased Stem Cell Repopulation of Traumatized Tissue

A mouse model is used to evaluate homing and integration of bone marrow derived stem cells into traumatized tissue All marrow donors are adult male mice (8-10 weeks of age), and all recipient mice are adult females (8-10 weeks of age). Two groups of mice are evaluated. One group of sub-lethally irradiated recipients receive $6 \times 10^6$ nucleated donor cells via injection in the tail vein and allowed 2 weeks of recovery. The animals are then lightly traumatized by thin needle insertion into hind leg muscle, heart, and brain. All animals receive normal feed throughout the study. In the second group, female mice are treated identically as the first group, but are fed a diet that includes 0.5 to 15% w/v of the selectin-ligand containing fraction of AFA.

Two mice are sacrificed prior to trauma to evaluate baseline levels of male-derived cells. Subsequently, mice are sacrificed at the following time points: 1 week, 2 weeks, 3 weeks, and 4 weeks. Two mice are sacrificed for each time point, except for the 2 week time point, where 6 mice are sacrificed from each group. Hind leg muscle, heart, and brain tissue is isolated from the sacrificed animals. Sections are cut through the traumatized areas, and stained for male-derived cells using either cell surface marker analysis for the expression of the Hy antigen or by fluorescence in situ hybridization using probes for the Y chromosome. Alternatively, a GFP-expressing transgenic donor mouse will be used (similar to Example #4).

Data obtained demonstrate the effect of consuming the selectin-ligand containing fraction of AFA on the speed of stem cell recruitment following trauma.

Example 12

Case Report for Tissue Repair

A subject was a body builder who had a car accident three years ago. A car hit her car in the door on the driver's side and several muscles were torn in her hip and thigh. She underwent a series of surgeries to re-attach the severed muscles. In spite of the successful surgeries, the muscle damage was so severe that she remained with a constant pain and could not resume her weight lifting training, as even a mild training session would be followed by swelling and pain, which would prevent walking for several days.

She tried many anti-inflammatory drugs, but after 18 months she still could not train. She began consuming the blue green algae fraction containing a selectin ligand. Two weeks later, she reported being able to return to the gym, and after two months of consumption, she had resumed normal training, indicating extensive repair of muscle tissue.

Example 13

Case Report for Tissue Repair

A 55 year old subject went for a sixth hip replacement—fourth on the left side. Generally, there was a very poor prognosis and enormous difficulties involved.

The orthopedic surgeon rebuilt the pelvis and acetabeum. However, prior to the surgery the subject was informed by the medical staff that there was no way for the body to produce new bone necessary for the long term success of the procedure. It was presented that if the subject was to get bone growth it likely would be less than required for healing.

The subject was provided with the blue-green algae fraction containing L-selectin shortly after the surgery. The new, strong bone growth appeared quickly and recovery was rapid. The subject reported that they no longer needed crutches and was able to be on full weight bearing status in 6 weeks—compared to 6 months with the subject's previous surgery. The subject reported that the accelerated healing was confirmed in every check-up. The subject also reported that the bone surrounding their right hip that had a revision done in early 80's was found very strong. This was considered exceptional.

Example 14

Case Report

A young girl was diagnosed at the age of three with infantile muscular dystrophy. She was unable to walk. She was very frail, and frequently experienced pneumonia, which each time resulted in confinement to bed for 8-10 days. She was on conventional therapy for muscular dystrophy for six months, but this resulted in no change. She started consuming *Spirulina*, which to some extent improved her immune function as she experienced less frequent and less severe pneumonias. She then started consuming the blue green algae fraction containing a selectin ligand (Extract A). After two weeks she started taking her first steps. After three months she was walking. She had no more pneumonia.

The disease is an inherited disease, and several family members with same disease—but further degenerated—also started consuming the algae fraction (Extract A). These individuals reported that they experienced benefits of consuming this fraction.

Example 15

Human Studies

A triple-blinded, randomized, placebo-controlled study on human subjects was conducted on the effect of various AFA extracts on the numbers of circulating stem cells. The following methods were used in these studies:

Consumables: Four consumables were tested. Two were liquid, and two were encapsulated. Neither the volunteers, nor the person administering the substance, nor the lab staff performing data analysis knew which substance was being administered at a given study day.
1. LSL: Extract A, an AFA fraction enriched in the L-selectin ligand. One gram of the fraction concentrated in L-selectin ligand (LSL) was mixed in 40 ml of water and served to study subjects in a paper cup.
2. Migratose (MGT): The fraction known to contain the bioactive compound responsible for the migration of immune and stem cells was obtained by extracting liquid AFA with 10% ethanol at 50° C. for one hour. The solution was centrifuged and the supernatant was dried using RW. This product has been internally named Migratose (MGT). Migratose (150 mg) was blended with 250 mg placebo and administered in a vegetable capsule.
3. StemEnhance (SE): StemEnhance is a blend of LSL and Migratose. One gram of StemEnhance was mixed in 40 ml of water and served to study subjects in a paper cup.
4. Placebo: The placebo consisted of 400 mg green-dyed, finely ground potato flakes encapsulated in vegetable capsules. The appearance was identical to that of capsules containing Migratose.

Subjects: A total of 19 people were interviewed from regular blood-donation healthy volunteers. The following exclusion criteria were used:

Under 20 or over 65 years of age

Pregnancy

Severe asthma and allergies requiring daily medication

Any known chronic illness or previous/current venereal disease

Frequent recreational drug use

Impaired digestive function (including previous major gastrointestinal surgery).

Of the people interviewed, 14 met the study criteria and were willing to participate. Among the 14, three were subsequently excluded part way through the study due to non-compliance. Among the remaining 11 volunteers, six went through four study days each, such that data was obtained for all four consumables on the same person. The remaining five volunteers were able to participate in three study days each.

Subjects were scheduled for arrival on the same weekday on four successive weeks during a two month period. Subjects were scheduled on the same weekday for greater consistency in the data. They were instructed to have a good night's sleep before each study day, and to eat the same type of bland breakfast on each study day.

Upon arrival, the volunteers were seated in quiet areas away from each other, to discourage chatting and produce a quiet environment (there were no disturbances such as phones, door bells, talking among lab staff). The volunteers were instructed to remain quiescent, comfortably sitting in a chair, for one hour. Movement was restricted to slow walking to the bathroom, if needed. After one hour, the baseline blood sample was drawn. Immediately after drawing the baseline sample, a consumable was provided. The volunteers were instructed to remain quiescent for the whole duration of the experiment. Blood samples were later drawn 30, 60 and 120 minutes after ingestion of the consumable.

Every day, upon arrival to the laboratory, volunteers filled a questionnaire giving a daily assessment of their general conditions. This questionnaire was intended to identify any instance for which data points might have to be eliminated due to extraordinary circumstances. The following criteria were used for eliminating data points:

Lack of sleep

Stimulants within 2 hours of arrival

Stress.

Assessment of circulating stem cells: At each time point, 5 ml blood was drawn into heparin, and 2 ml blood was drawn into EDTA. The blood vials were placed on a rocking plate until use. The blood drawn into EDTA was used for obtaining a complete blood count (CBC) using a Coulter counter (Micro Diff II, Beckman Coulter). All CBCs were performed within an hour of drawing the sample. All CBCs were performed in triplicate.

The heparinized blood was used for purification of the peripheral blood mononuclear cell fraction by gradient centrifugation, and processed for immunostaining and flow cytometry. The stem cell markers CD34-FITC (clone 8G12) and CD133-PE were used for two-color immunofluorescence. Staining of all samples with CD34-FITC/CD133-PEW was performed in triplicate. Appropriate isotype controls were used in parallel samples. Positive controls for each donor included CD45 and CD14. Stained cells were fixed in 1% formalin and acquired by flow cytometry immediately. Files of 200,000 events were collected on each sample.

Since the cells used for immunostaining did not include the granulocyte population, the acquisition of 200,000 events included more stem cells than if whole blood had been used. The use of the peripheral blood mononuclear cell fraction thus allows collection of data with higher numbers of stem cells, giving a better statistical weight to observed differences in stem cell numbers.

Staining for CD14 was performed in parallel samples, as not to interfere with the analysis of CD34 and CD133. Flow cytometric analysis was performed using the CellQuest Pro software (Becton Dickinson).

Figure 9:
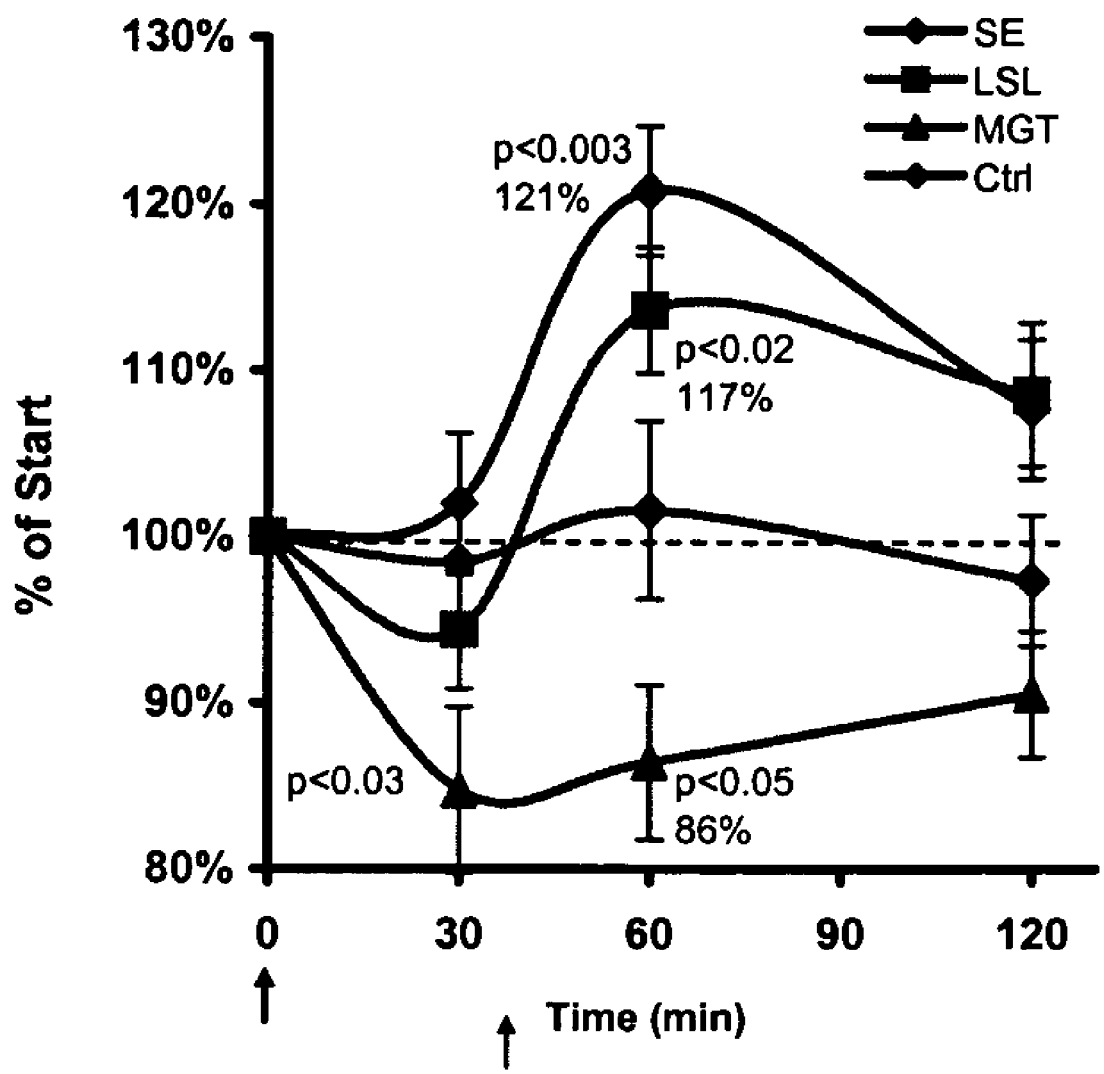
FIG. 9 is a line graph showing the time course of the number of CD34+ cells in human peripheral blood after consumption (arrow) of L-selectin ligand (LSL), migratose (MGT), stem enhanced combination (SE) or a placebo (labeled Ctrl). L-selectin ligand (LSL) is an extract of *Aphanizomenon flos aquae* (AFA) enriched for the L-selectin ligand. For the subjects treated with LSL, one gram of the extract concentrated in L-selectin ligand (see the examples section) was mixed in 40 ml of water and consumed by the subject. Migratose (MGT) is an extract wherein liquid *Aphanizomenon flos aquae* (AFA) was extracted with 10% ethanol at 85° C. for three hours. The solution was centrifuged and the supernatant was dried using RW. For administration, 150 mg of the dried product was blended with 250 mg of a carrier, encapsulated in a vegetable capsule and consumed by the subjects. Stem enhance combination (SE) was a blend of LSL and MGT, as described above. One gram of SE was mixed in 40 ml of water and consumed by the subjects. The control was 400 mg of finely ground potato flakes encapsulated in vegetable capsules.

The following results were obtained:

Consumption of SE and LSL led to an increase in the number of circulating CD34+ cells (see FIG. 9), while MGT led to a decrease in the number of circulating CD34+ cells. After consumption of placebo small changes that were not statistically significant were. With both SE and LSL a number of volunteers showed a tendency for an initial transient decrease in the number of CD34+ cells; this observation was greater for LSL though did not reach significance. At sixty minutes after consumption, SE ($p<0.003$) and LSL ($p<0.02$) triggered a significant increase in the number of CD34+ cells. However, MGT triggered a significant decrease ($p<0.03$).

In a subsequent part of the data analysis, each volunteer's responses to AFA extracts were normalized to the same person's response to placebo. This was done by subtracting the percentage change obtained with the placebo from the percentage change obtained with the extract. This was done for all three consumables. This procedure did not increase the magnitude or significance of the responses; the pattern obtained was similar to FIG. 9.

Another part of the data analysis focused on the maximum percent change for each consumable compared to placebo. The rationale for this analysis is that the absorption of bioactive compounds, delivery to target organs, and time to generate a quantifiable physiological response may be different depending on each volunteer's overall physiology. This analysis method minimizes differences in individual response times and allows a comparison of the extent of change, irrespective of whether the maximum change was observed at 30 or 60 minutes. Based on this method a 24±5% increase in the number of circulating stem cells with SE and a 24±2% decrease with MGT was found. A median response of 27% and 77%, respectively, for SE and MGT was found.

The timeframe to reach maximal response appears to be of no more than a few weeks. To avoid a potential confounding factor in the data, most of the studies were performed on samples from subjects who regularly consumed AFA. In the present study, only one subject was not a regular consumer of AFA. This one subject showed no noticeable increase in CD34+ cells mobilization. It should be noted that this volunteer was removed from the analysis. As it was only a single subject who did not regularly consume AFA, the samples obtained from the subject could not be used for a relevant statistical analysis. In addition, one complication in this type of protocol is the fact that individuals do not all mobilize according to a similar time frame, and thus there may be an under-estimation of the actual peak of mobilization. The response to placebo showed variations, though such fluctuations did not reach statistical significance. Nevertheless, these fluctuations appear to be real and suggest that a better understanding of the daily cycling of circulating CD34+ could be of use in designing future studies.

This study confirmed that SE and LSL, both of which include a dried aqueous extract enriched for a selectin ligand, are effective at mobilizing bone marrow stem cells by increasing the number of circulating CD34+ cells. The data collected in this study show that SE increases the number of circulating stem cells by up to 35%.

It will be apparent that the precise details of the methods or compositions described may be varied or modified without departing from the spirit of the described invention. We claim all such modifications and variations that fall within the scope and spirit of the claims below.

The invention claimed is:

1. A composition comprising a first and a second component of *Aphanizomenon flos aquae*, wherein the first component consists of a dried form of a solvent extract of fresh, dehydrated, or preserved *Aphanizomenon flos aquae*, wherein the extract comprises a L-selectin ligand that binds specifically to L-selectin and inhibits fucoidan-mediated expression of the CXCR4 receptor, and where the solvent consists of water or buffered saline; and
   wherein the second component consists of a dried form of a second solvent extract of fresh, dehydrated, or preserved *Aphanizomenon flos aquae*, wherein the second solvent comprises ethanol.

2. A composition comprising a therapeutically effective amount of the composition of claim 1 in a pharmacologically acceptable carrier.

3. The composition of claim 2, wherein the second solvent extract is produced by suspending dried *Aphanizomenon flos aquae* in about 10 to about 20 percent ethanol at about 50° C. to about 60° C.

4. The composition of claim 2, comprising 1 gram to about 2 grams of the first component of *Aphanizomenon flos aquae*, and about 100 milligrams to about 500 milligrams of the second component of *Aphanizomenon flos aquae*.

5. The composition of claim 4, comprising about 1 gram of the first component of *Aphanizomenon flos aquae*, and about 150 milligrams of the second component of *Aphanizomenon flos aquae*.

6. The composition of claim 5, produced by the process of
   contacting a first amount of *Aphanizomenon flos aquae* in a solvent consisting of water or phosphate buffered saline for about half an hour to about 12 hours to produce a first extract;
   removing solid material from the first extract;
   drying the first extract to produce a solid composition comprising a L-selectin ligand;
   incubating a second amount of *Aphanizomenon flos aquae* in 10 percent ethanol at about 50° C. for about one hour to produce a second extract;
   removing solid material from the second extract;
   drying the second extract to produce a solid form of the second extract; and
   mixing a therapeutically effective amount of the solid composition comprising the L-selectin ligand and a therapeutically effective amount of the solid form of the second extract.

7. A composition comprising about 1 gram of a first component of *Aphanizomenon flos aquae* and about 150 milligrams of a second component of *Aphanizomenon flos aquae*, wherein the first component consists of a dried form of a first solvent extract of fresh, dehydrated, or preserved *Aphanizomenon flos aquae*, wherein the first solvent extract comprises a L-selectin ligand that binds specifically to L-selectin and inhibits fucoidan-mediated expression of the CXCR4 receptor, and where the first solvent consists of water or buffered saline; and wherein the second component consists of a dried form of a second solvent extract of fresh, dehydrated, or preserved *Aphanizomenon flos aquae*, wherein the second solvent comprises about 10 percent to about 20 percent ethanol.

8. The composition of claim 7, where the first solvent consists of water.

9. The composition of claim 7, where the first solvent consists of buffered saline.

10. The composition of claim 7, wherein the second solvent comprises about 10 percent ethanol.

11. The composition of claim 7, wherein the second solvent comprises about 20 percent ethanol.

12. The composition of claim 7, wherein the composition is a solid.

13. The composition of claim 10 wherein the solid is encapsulated.

14. A liquid composition comprising 1 gram of the composition of claim 7 dissolved in water.

* * * * *

UNITED STATES PATENT AND TRADEMARK OFFICE
CERTIFICATE OF CORRECTION

| | |
|---|---|
| PATENT NO. | : 7,651,690 B2 |
| APPLICATION NO. | : 11/473875 |
| DATED | : January 26, 2010 |
| INVENTOR(S) | : Jensen et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,651,690 B2 | |
| APPLICATION NO. | : 11/473875 | |
| DATED | : January 26, 2010 | |
| INVENTOR(S) | : Jensen and Drapeau | |

It is certified that error appears in the above-identified patent and that said Letters Patent is hereby corrected as shown below:

On the Cover:
    Under OTHER PUBLICATIONS, Column 2, "cerbellar" should read --cerebellar--.
    Under OTHER PUBLICATIONS, Page 2, Column 1, "phycodyanin" should read --phycocyanin--.
    Under OTHER PUBLICATIONS, Page 2, Column 2, "Hepatotooxicty" should read --Hepatotoxicity--.
    Under ABSTRACT, "enriched form" should read --enriched for--.

In the Specification:
    Column 1, line 51, "be use" should read --be used--.
    Column 1, line 63, "15; 78" should read --15, 78--.
    Column 3, line 18, "monoclytes," should read --monocytes,--.
    Column 5, line 40, "cell," should read --cells,--.
    Column 6, lines 6 and 7, "the component is a component is a phytochemical." should read --the component is a phytochemical.--.
    Column 6, line 52, "of from" should read --or from--.
    Column 7, line 35, "to the a" should read --to a--.
    Column 7, line 45, "hematopeoietic" should read --hematopoietic--.
    Column 10, line 4, "glexibility" should read --flexibility--.
    Column 10, line 5, "specification" should read --specification.--.
    Column 11, line 21, "tracking" should read --trafficking--.
    Column 13, line 16, "1999)." should read --1999.--.
    Column 13, line 22, "general" should read --generally--.
    Column 14, line 8, "extracted" should read --extract--.
    Column 14, line 37, "in which the" should read --including the--.
    Column 14, lines 46 and 47, "can cleaved" should read --can be cleaved--.
    Column 15, line 43, "one more accessory" should read --one or more accessory--.
    Column 16, line 25, "85 ° C. is applied" should read --85 ° C., and is applied--.
    Column 16, line 26, "as a temperature" should read --as at a temperature--.

Signed and Sealed this
Twenty-second Day of February, 2011

David J. Kappos
*Director of the United States Patent and Trademark Office*

CERTIFICATE OF CORRECTION (continued)

Column 16, line 39, "form" should read --from--.
Column 17, line 21, "of from" should read --from--.
Column 17, line 24, "form" should read --from--.
Column 18, line 44, "may about" should read --may be about--.
Column 19, line 15, "Extract A" should read --Extract A.--.
Column 21, line 46, "This experiments" should read --The experiment--.
Column 21, line 63, "(Beckton-Dickinson" should read --(Becton-Dickinson--.
Column 22, line 14, "that" should read --than--.
Column 24, lines 17 and 18, "not a Found" should read --not Found--.
Column 26, line 8, "tissue" should read --tissue.--.
Column 29, line 20, "significant were." should read --significant were observed.--.
Column 29, line 24, "(p<0.02" should read --(p<0.02)--.

<u>In the Claims:</u>
Column 32, line 5, Claim 13, "claim 10" should read --claim 12--.